US010844110B2

(12) United States Patent
Klausen et al.

(10) Patent No.: US 10,844,110 B2
(45) Date of Patent: Nov. 24, 2020

(54) O-LINKED GLYCOFORMS OF POLYPEPTIDES AND METHOD TO MANUFACTURE THEM

(71) Applicant: Novo Nordisk HealthCare AG, Zurich (CH)

(72) Inventors: Niels Kristian Klausen, Gentofte (DK); Daniel E. Rasmussen, Koebenhavn OE (DK)

(73) Assignee: Novo Nordisk Healthcare AG, Zurich (CH)

( * ) Notice: Subject to any disclaimer, the term of this patent is extended or adjusted under 35 U.S.C. 154(b) by 236 days.

(21) Appl. No.: 15/727,912

(22) Filed: Oct. 9, 2017

(65) Prior Publication Data

US 2018/0057566 A1  Mar. 1, 2018

Related U.S. Application Data

(63) Continuation of application No. 11/579,401, filed as application No. PCT/EP2005/052024 on May 3, 2005, now abandoned.

(60) Provisional application No. 60/577,613, filed on Jun. 7, 2004.

(30) Foreign Application Priority Data

May 4, 2004 (DK) .................................. 2004 00712
Jun. 4, 2004 (DK) .................................. 2004 00882

(51) Int. Cl.
C07K 14/745 (2006.01)

(52) U.S. Cl.
CPC .................................. C07K 14/745 (2013.01)

(58) Field of Classification Search
None
See application file for complete search history.

(56) References Cited

U.S. PATENT DOCUMENTS

| | | | |
|---|---|---|---|
| 4,055,635 A | 10/1977 | Green et al. |
| 4,088,538 A | 5/1978 | Schneider |
| 4,179,337 A | 12/1979 | Davis et al. |
| 4,385,260 A | 5/1983 | Watts |
| 4,412,989 A | 11/1983 | Iwashita et al. |
| 4,414,147 A | 11/1983 | Klibanov et al. |
| 4,496,689 A | 1/1985 | Mitra |
| 4,806,595 A | 2/1989 | Noishiki et al. |
| 4,925,796 A | 5/1990 | Bergh et al. |
| 5,154,924 A | 10/1992 | Friden |
| 5,182,107 A | 1/1993 | Friden |
| 5,352,670 A | 10/1994 | Venot et al. |
| 5,374,541 A | 12/1994 | Wong et al. |
| 5,405,753 A | 4/1995 | Brossmer et al. |
| 5,432,059 A | 7/1995 | Bean et al. |
| 5,527,527 A | 6/1996 | Friden |
| 5,545,553 A | 8/1996 | Gotschlich |
| 5,614,184 A | 3/1997 | Sytkowski et al. |
| 5,621,039 A | 4/1997 | Hallahan et al. |
| 5,672,683 A | 9/1997 | Friden et al. |
| 5,716,812 A | 2/1998 | Withers et al. |
| 5,728,554 A | 3/1998 | Bayer et al. |
| 5,833,988 A | 11/1998 | Friden |
| 5,834,251 A | 11/1998 | Maras et al. |
| 5,876,980 A | 3/1999 | DeFrees et al. |
| 5,922,577 A | 7/1999 | Defrees et al. |
| 5,969,040 A | 10/1999 | Hallahan et al. |
| 5,977,307 A | 11/1999 | Friden et al. |
| 6,013,620 A | 1/2000 | Turecek et al. |
| 6,015,555 A | 1/2000 | Friden |
| 6,030,815 A | 2/2000 | DeFrees et al. |
| 6,037,452 A | 3/2000 | Minamino et al. |
| 6,100,061 A | 8/2000 | Reiter et al. |
| 6,166,183 A | 12/2000 | Ishikawa et al. |
| 6,183,738 B1 | 2/2001 | Clark |
| 6,692,931 B1 | 2/2004 | Reutter et al. |
| 6,777,390 B1 | 8/2004 | Matthiessen et al. |
| 7,265,085 B2 | 9/2007 | DeFrees et al. |
| 7,338,933 B2 | 3/2008 | DeFrees et al. |
| 2002/0137134 A1 | 9/2002 | Gemgross |
| 2005/0250678 A1 | 11/2005 | DeFrees et al. |

FOREIGN PATENT DOCUMENTS

| | | |
|---|---|---|
| AU | 2004/222625 A1 | 9/2004 |
| DK | PA200301646 | 11/2003 |
| JP | 2000-302689 | 10/2000 |
| JP | 2001-029095 A | 2/2001 |
| JP | 2002-518411 A | 6/2002 |
| JP | 2004-510786 | 4/2004 |
| JP | 2009-506764 A | 2/2009 |
| WO | 87/00056 A1 | 1/1987 |
| WO | 87/05330 A1 | 9/1987 |
| WO | 89/10134 A1 | 11/1989 |
| WO | 90/07572 A1 | 7/1990 |
| WO | 92/18135 A1 | 10/1992 |
| WO | 94/05332 A2 | 3/1994 |

(Continued)

OTHER PUBLICATIONS

Scharrer (Hemophilia vol. 5, pp. 253-259). (Year: 1999).*
Declaration of Neils Kristian Klausen, Jun. 15, 2011.
Ohta et al., "Usefulness of LC/MS as Equality and Homogeneity of Glycoprotein Product", Summaries of Symposia of the Annual Meeting of the Pharmaceutical Society of Japan, Mar. 5, 2001, vol. 121, No. 4, p. 137.
Hayakawa, "Scienc of Evaluating the Quality and Safety of Biotechnological Products", PDA Journal of GMP Validation in Japan, 2001, vol. 3, No. 2, p. 57-66.

(Continued)

Primary Examiner — Robert A Zeman
(74) Attorney, Agent, or Firm — Jianjie Hu

(57) ABSTRACT

The present invention relates to compositions comprising glycoproteins having altered patterns of O-linked glycosylation, in particular Factor VII, Factor IX, and methods for making these.

10 Claims, 7 Drawing Sheets

Specification includes a Sequence Listing.

(56) References Cited

FOREIGN PATENT DOCUMENTS

| | | |
|---|---|---|
| WO | 94/15625 A1 | 7/1994 |
| WO | 95/02421 A1 | 1/1995 |
| WO | 95/18232 A1 | 7/1995 |
| WO | 96/07753 A1 | 3/1996 |
| WO | 96/32491 A1 | 10/1996 |
| WO | 96/40731 A1 | 12/1996 |
| WO | 98/31826 A1 | 7/1998 |
| WO | 98/58964 A1 | 12/1998 |
| WO | 99/00150 A2 | 1/1999 |
| WO | 99/22764 A1 | 5/1999 |
| WO | 99/66031 A2 | 12/1999 |
| WO | 00/72873 | 12/2000 |
| WO | 2001/049830 A2 | 7/2001 |
| WO | 2001/060411 A1 | 8/2001 |
| WO | 01/88117 A2 | 11/2001 |
| WO | 2001/082943 A2 | 11/2001 |
| WO | 02/02597 A2 | 1/2002 |
| WO | 2002/013843 A2 | 2/2002 |
| WO | 2002/013873 A2 | 2/2002 |
| WO | 02/17957 | 3/2002 |
| WO | 2002/029025 A2 | 4/2002 |
| WO | 02/074806 A2 | 9/2002 |
| WO | 03/02524 A2 | 1/2003 |
| WO | 2003/031464 A2 | 4/2003 |
| WO | 03/046150 A2 | 6/2003 |
| WO | 03/55511 A1 | 7/2003 |
| WO | 03/055512 A1 | 7/2003 |
| WO | 2004/000366 A1 | 12/2003 |
| WO | 2004/082708 A2 | 9/2004 |
| WO | 2004/110469 A2 | 12/2004 |
| WO | 2005/014035 A2 | 2/2005 |
| WO | 2005-111225 A1 | 11/2005 |

OTHER PUBLICATIONS

Kawasaki, "Mass Spectrometric Analysis of Glycoprotein", Summary of Symposia of Annual Meeting of Pharma Society, 2004, vol. 124, No. 1, p. 111.
Bjoern, S, et al. Journal of Biological Chemistry, Human Plasma and Recombinant Factor III; Characterization of O-Glycosylation at Serine Residues 52 and 60 and Effects of Site-Directed Mutagenesis of Serine 52 to Alanine, 1991 vol. 266 Part 17 pp. 11051-11057.
Burton and Harding, Journal of Chromatography, Hydrophobic Charge Induction Chromatography: Salt Independent Protein Adsorption and Facile Elution With Aqueous Buffers, 1998, vol. 814 p. 71-81.
Cumming, Dale A, Glycobiogoly, Glycosylation of Recombinant Protein Therapeutics: Control and Functional Implications 1991, vol. 1 Part 2 pp. 115-130.
Grebenau et al, Molecular Inmunology, 1992, vol. 29 Part 6 pp. 751-758.
Iino, M et al, Archives of Biochemistry and Biophysics, Functional Consequences of Mutations in Ser-52 and Ser-60 in Human Blood Coagulation Factor V8II 1 1998 vol. 352 Part 2 pp. 182-192.
Jurlander et al, Seminars in Thrombosis and Hemostasis, Recombinant Activated Factor VII (RFVIIA): Characterization, Manufacturing, and Clinical Development 2001, vol. 27, Part 4, pp. 373-383.
Klausen et al, Molecular Biotechnology, Analysis of the Site-Specific Asparagine-Linked Glycosylation of Recombinant Human Coagulation Factor VIIA by Glycosidase Digestions, Liquid Chromatography, and Mass Spectrometry 1998 vol. 9 pp. 195-204.
Klausen, NK et al, Journal of Chromatography, Analysis of the Glycoforms of Human Recombinant Factor VIIA by Capillary Electrophoresis and High-Performance Liquid Chromatography 1995 vol. 718 Part 1 pp. 195-202.
Nishimura, H et al, Journal of Biological Chemistry, Identification of Disaccharide (XYL-GLC) and a Trisaccharide (XY12-GLC) O-Glycosidically Linked to a Serine Residue in the First Epidermal Growth Factor-Like Domain Human Factors VII and IX and . . . 1989 vol. 264 Part 34 pp. 20320-20325.

Shao et al, Glycobiology, O-Glycosylation of EGF Repeats: Identification and Initial Characterization of a UDP-Glucose: Protein O-Glucosyltransferase 2002 vol. 12 Part 11 pp. 763-770.
Thim et al, Biochemistry, Amino Acid Sequence and Post-translational Modifications of Human Factor VII, From Plasma and Transfected Baby Hamster Kidney Cells 1988 vol. 27 pp. 7785-7793.
Mollerup et al., Biotechnology and Bioengineering, 1995, vol. 48, pp. 501-505.
Daniel Rasmussen, 2007 HIC-RPC Conference (Mar. 2007—Interlaken, Switzerland).
Machine translation of WO 9966031, pp. 1-4. Accessed Mar. 4, 2009.
Bolt, Gert et al., Glycobiology, Posttranslational N-Glycosylation Takes Place During the Normal Processing of Human Coagulation Factor VII, 2005, vol. 15 Part 5 pp. 541-547.
Cooper, HA et al,. Journal of Clinical Investigation, Effects of Thrombin Treatment of Preparations of . . . 1975 vol. 56 Part 3 pp. 751-760.
Josic, D et al., Journal of Chromatography, Preparation of Vitamin K-Dependent Proteins, Such as . . . 2003, vol. 730 Parts 1-2, pp. 183-197.
Soenderkaer, S, et al., Effects of Sucrose on RFVIIA Aggregation and Methionine Oxidation, European Journal of Pharmaceutical Sciences, 2004, vol. 21, No. 5, pp. 597-606.
Second Declaration of Nields Kristian Klausen Dated Nov. 6, 2012.
Iwanaga et al., Fibrogen, Thrombosis, Coagulation and Fibronolysis, a New Trisaccharide Sugar Chain Linked to a Serine Residue in the First EGF-Like Domain of Clotting Factors VII and IX and Protein Z, 2012 pp. 121-131.
Ito et al. "Synthesis of Biavtive Sialosides." Pure and Applied Chem., 1993, vol. 65, No. 4 pp. 753-762.
Gross, HJ. "Florescent CMP-sialic acids as a tool to study the specificty of the CMP-sialic acid carrier and the glycoconjugate sialylation in pemetilized cells." Eur J Biochem. Jan. 15, 1992. 203(1-2) pp. 269-275.
Abuchowski et al 1977. J Biol Chem 252: pp. 3578-3586.
Abuchowiski et al. 1984 Cancer Biochem Biophys. vol. 7 pp. 175-186.
Ailor et al. 1999, Glycobiology vol. 10. pp. 837-847.
Altmann et al. 1999, Glycoconjugate J vol. 16. pp. 109-123.
Aplin et al. 1981 CRC Crit Rev Biochem. vol. 131 pp. 25-33.
Beauchamp et al. 1983 Anal Biochem. vol. 131 pp. 25-33.
Berger et al. 1988, Blood vol. 71 pp. 1641-1647.
Berg-Fassman et al. 1993. J Biol. Chem vol. 268 pp. 14861-14866.
Bhadra et al. 2002 Pharmazie. vol. 57 pp. 5-29.
Bickel et al. 2001 Adv Drug Deliv Rev. vol. 46 pp. 247-279.
Bhatia et al. 1989 Anal Biochem vol. 178 pp. 408-413.
Bijsterbosch et al. 1996 Eur J Biochem. vol. 237 pp. 344-349.
Biome et al. 1995 Endocrinology vol. 136 pp. 2635-2640.
Boissel et al 1993 J Biol Chem. vol. 268 pp. 15983-15993.
Bouizar et al 1986 Eur J Biochem vol. 155 pp. 141-147.
Boyd et al 1995 Mol Immunol vol. 32 pp. 1311-1318.
Browning et al. 1989 J Immunol. vol. 143 pp. 1589-1867.
Buckman et al. 1981 Makromol Chem vol. 182. pp. 1379-1384.
Burns et al. 2002 Blood vol. 99 pp. 4400-4405.
Butnev et al 1998. Biology of Reproduction vol. 58 pp. 458-469.
Byun et al 1992. ASAIO Journal M649-M653.
Casares et al 2001, Nature Biotech vol. 19 pp. 142-147.
Chaffee et al. 1992 J Clin Invest vol. 89 pp. 1643-1651.
Charter et al. 2000. Glycobiology vol. 10. pp. 1049-1056.
Chern et al. 1991, Eur J Biochem vol. 202 pp. 225-229.
Chiba et al 1995, Biochem J vol. 308 pp. 405-409.
Chrisey et al 1996 Nucleic Acids Res vol. 24 pp. 3031-3039.
Conradt et al. 1987 J Bio Chem vol. 262 pp. 14600-14605.
Crout et al 1998, Curr Opin Chem Biol vol. 2 pp. 98-111.
Delgado et al. 1992 Critical Reviews in Therapeutic vol. 9 pp. 249-304.
Delgado et al. 1990 Biotechnol Appl Biochem vol. 12 pp. 119-128.
Dunn et al 1991. Eds Polymeric Drugs and Drug Delivery Systems. col. 469 American CHemical Society, Washington DC.
Dwek et al. 1995 J Anat vol. 187 pp. 279-292.
Eavarone et al. 2000 J Biomed Mater Res vol. 51 pp. 10-14.

(56) References Cited

OTHER PUBLICATIONS

Fibi et al. 1995 Cells Blood vol. 85 vol. 1229-1236.
Fischer et al 1998 Thrombosis Research vol. 89 pp. 147-150.
Flynn et al 2000 Curr Opin Oncol vol. 12 pp. 574-581.
Garnett et al. 2002 Advanced Drug Delivery Reviews vol. 53 pp. 171-216.
Gillis et al. 1988 Behring Inst Mitt. August Vol. 83 pp. 1-7.
Grodberg et al. 1993. Eur J Biochem. vol. 218. pp. 597-601.
Hall et al 2001 Methods in Molecular Biology. vol. 166 pp. 139-154.
Haneda et al. Carbohydr. Res, 1996, vol. 292 pp. 61-70.
Hang et al. 2001, J Am Chem Soc vol. 123 pp. 1242-1243.
Harris 1985 Macronol Chem Phys vol. C25. pp. 325-373.
Hellstrom et al 2001 Method in Molecular Biology vol. 166 pp. 3-16.
Hermanson et al 1993 Immobilized Affinity Ligand Techniques, Academic Press.
Hermanson 1996 Bioconjugate Techniques, Academic Press, San Diego.
Hilles et al. 2002 American Biotechnology Laboratory Pgs vol. 20 p. 30.
Hollister et al 2001 Glycobiology vol. 11 pp. 1-19.
Hounsell et al. 1996 Glycoconj J vol. 13 pp. 19-26.
Huang et al. 1984 Proc Natl Acad Sci USA vol. 81 pp. 2708-2712.
Ichikawa et al. 1992 J Am Chem Soc vol. 114 pp. 9283-9298.
Inoue et al. 1995 Biotechnology Annual Review vol. 1 pp. 297-313.
Ito et al. 1993 Pure Appl Chem Soc vol. 114 pp. 9283-9298.
Jackson et al 1987 Anal Biochem vol. 165 pp. 114-127.
Jarvis et al. 1998 Curr Opin Biotechnol vol. 9 pp. 528-533.
Joppich et al 1979 Markromol Chem vol. 180 pp. 1381-1384.
Joshi et al 1990 J biol Chem vol. 265 pp. 14518-14525.
Jung et al 1983 Biochem Biophys Acta vol. 761 pp. 152-162.
Kalsner et al 1995 Clycoconj J vol. 12 pp. 360-370.
Kasina et al 1998 Bioconjugate Chem vol. 9 pp. 108-117.
Katre et al 1987 Proc Natl Acad Sci USA vol. 84 pp. 1487-1491.
Keppler et al 2001 Glycobiology vol. 11 pp. 11R-18R.
Kitamura et al 1990 Biochem Biophysi Res Commun vol. 28 pp. 1387-1394.
Kitamura et al 1991 Cancer Res vol. 51 pp. 4310-4315.
Kodama et al 1993 Tetrahedron Lett vol. 34 pp. 6419-6422.
Koeller et al 2000 Nature Biotechnology vol. 18 pp. 835-841.
Koide et al 1983 Biochem Biophys Res Commun vol. 111 pp. 659-667.
Kreitmann 2001 Current Pharmaceutical Biotechnology vol. 2 pp. 313-325.
Lai et al 1986 J Biol Chem vol. 261 pp. 3116-3121.
Lee et al 1989 Biochemistry vol. 28 pp. 1856-1861.
Li et al 2002 Trends in Pharmcological Sciences vol. 23 pp. 206-209.
Li et al 2002 Medicinal Research Reviews vol. 22 pp. 225-250.
Lord et al 2001 Clin Cancer Res vol. 7 pp. 2085-2090.
Lougheed et al 1999 J Biol Chem vol. 274 pp. 37717-37722.
Lucklow et al 1993 Curr Opin Biotechnol vol. 4 pp. 564-572.
Liu et al 1996 Chem Eur J vol. 2 pp. 1359-1362.
Lund et al 1995 FASEB J vol. 9 pp. 115-119.
Lund et al 1996 J Immunol vol. 157 pp. 225-263.
Mahal et al 1997 Science vol. 276 pp. 1125-1128.
Maras et al 2000 J Biotechnol vol. 77 pp. 255-263.
Miller et al 1993 Curr Opin Genet Dev vol. 3 pp. 97-101.
Min et al 1996 Endocr vol. 43 pp. 585-593.
Mistry et al 1996 Lancet vol. 348 pp. 1555-1559.
Morimoto et al 1996 Glycoconjugate J vol. 13 pp. 1013-1020.
Nilsson et al. 1984 Methods Enzymol vol. 104 pp. 56-69.
O'Connell et al 1992 J Biol Chem vol. 267 pp. 25010-25018.
Olson et al 1999 J Biological Chem vol. 274 pp. 29889-29896.
Palacpac et al. 1999 PNAS USA vol. 96 pp. 4692-4697.
Park et al 1986 J Biol Chem vol. 261 pp. 205-210.
Paulson et al 1997 J Biol Chem vol. 252 pp. 8624-8628.
PEG Glucocerebrosidase, Internet Page from www.gaucher.org.uk/peg2.prg printed Jun. 21, 2002.
Zalipsky et al 1992 Chemistry: Biotechnical and Biomedical Applications, Plenum Press, New York.
Pyatak et al 1980 Res Commun Chem Pathol Pharmacol vol. 29 pp. 113-127.
Rambouille et al 1999 J Cell Biol vol. 112 pp. 3319-3330.
Reff et al 2002 Cancer Control vol. 9 pp. 152-166.
Sadler et al 1982 Methods in Enxymology vol. 83 pp. 458-514.
Saneyoshi et al 2001 Biology of Reproduction vol. 65 pp. 1686-1690.
Saxon et al 2000 Science vol. 287 pp. 2007-2010.
Schwientek et al 1994 Gene vol. 145 pp. 299-303.
Scouten 1987 Methonds in Enzymology vol. 135 pp. 30-65.
Shah et al 1996 J Pharm Scr vol. 85 pp. 1306-1311.
Singh et al 1996 Chem Commun vol. 8 pp. 993-994.
Song et al 2002 J Pharmcol Exp Ther vol. 301 pp. 605-610.
Srinivaschar et al 1989 Biochemistry vol. 28 pp. 2501-2509.
Takane et al 2000 J Pharmacology and Experimental Therapeutics vol. 294 pp. 746-752.
Takeda et al 1995 Trends Biochem Sci vol. 20 pp. 367-371.
Tanner et al 1987 Biochem Biophys Acta vol. 906 pp. 81-91.
Taylor et al 1991 Protein Immobilization Fundamentals and Applications Manual.
Thotakura et al 1987 Meth Enzymol vol. 138 pp. 350-359.
Tsuboi et al 2000 Archives of Biochemistry and Biophysics vol. 374 pp. 100-106.
Udenfriend et al 1995 Ann Rev Biochem vol. 64 pp. 593-591.
Ulloa-Aguirre et al 1999 Endocruine J vol. 11 pp. 205-215.
Uludag et al 2002 Biotechnol Pro vol. 18 pp. 604-611.
Urdal et al 1984 J Chromatog vol. 296 pp. 171-179.
Van Berkel et al 1996 Biochem J vol. 319 pp. 117-122.
Veronese et al 1985 Appl Biochem Biotech vol. 11 pp. 141-152.
Vocadlo et al 2000 in Carbohydrate Chemistry and Biology vol. 2.
Vyas et al 2001 Crit Rev Ther Drug Carrier Syst vol. 18 pp. 1-76.
Wang et al 1996 Tetrahedron Lett vol. 37 pp. 1975-1978.
Welhoner et al 1991 J Biol Chem vol. 226 pp. 4309-4314.
Witte K et al 1997 J Am Chem Soc vol. 119 pp. 2114-2118.
Woghiren et al 1993 Bioconjugate Chem vol. 4 pp. 314-318.
Wong et al 1982 J Org Chem vol. 47 pp. 5416-5418.
Wong et al 1992 Enzyme Microb Technol vol. 14 pp. 866-874.
Woods et al 1989 Eur J Cell Biol vol. 50 pp. 132-143.
Wright et al 1998 J Immunol vol. 160 pp. 3393-3402.
Wu et al 2002 J Druf Targeting vol. 10 pp. 239-245.
Xing et al 1998 Biochem J vol. 336 pp. 667-673.
Yamamoto et al 1998 Carbohydr Res vol. 305 pp. 415-422.
Yarema et al 1998 J Biol Chem vol. 47 pp. 31168-31179.
Yoshida et al 1999 Glycobiology vol. 9 pp. 53-58.
Zalipsku 1995 Bioconjugate Chem vol. 6 pp. 150-165.
Sichler et al. "Crystal Structres of Uninhibited Factor VIIa Link its Cofactor and Substrate-assisted Activation to Specific Interactions"Journal of Molecular Biology (2002) vol. 322(20): 591-603.
BeneFIX. www.benefix.com Accessed May 28, 2014.
Merchref et al. "Structural Investigations of Glycoconjugates at High Sensitivity" Chem Rev. 2002 vol. 102: 321-369.
Li, YuCai et al. "Separation of mistletoe lectins based on the degree of glycosylation using boronate affinity chromatography" J. Chromat (2001) vol. 925: 115-121.
Declaration of Professor Neil Kelleher, dated Apr. 19, 2013.
Yousefi, S et al. "Increased UDP-GlcNAc:Gal@1-3GalNAc-R (GlcNAc to GalNAc),8-1,6-N-Acetylglucosaminyltransferase Activity in Metastatic Murine Tumor Cell Lines" J Biol Chem vol. 266: 1772-1782 (1991).
Nicolaisen et al. "FVIIa derivatives obtained by autolytic and controlled cathepsin G mediated cleavage" FEBS Letter 1993 vol. 317(3): 245-9.
Declaration by Janus Karup dated Dec. 22, 2008.
Coagulation factor VIa, from www.drugs.com/cons/coagulation-factor-viia-intravenous.html, pp. 1-6. Accessed Jun. 19, 2014.
Don Oster, Potassium Chloride Vs. Sodium Chloride, Dec. 2000, from www.wqpmag.com/potassium-chloride-vs-sodium-chloride, pp. 1-3.
Naturally Occurring Amino Acids, from www.benjamin-mills.com/chemistry/amino-acids.htm, pp. 1-4, accessed Jul. 8, 2014.

(56) References Cited

OTHER PUBLICATIONS

Bajaj P. S. et al Isolation and Characterization of Human Factor VII Activation of Factor VI1 by Factor Xa, the Journal of Biological Chemistry, Year: 1981, vol. 256, No. 1, pp. 253-259.
Declaration and Curriculum Vitae of Dr. Mark Condina, signed Dec. 20, 2016.
Reply to Patentee's Appeal by Strawman Limited, dated Dec. 23, 2016.
Third Declaration by Niels Kristian Klausen, countersigned by Niels Vaever Hartvig, dated Jun. 29, 2017.
Persson et al., "Site-Directed Mutagenesis but not ?-Carboxylation of Glu-35 in Factor VIIa Affects the Association with Tissue Factor," FEBS Letters 385, 1996, pp. 241-243.
Kornfelt et al., "Oxidation of Methionine Residues in Coagulation Factor VIIa," Archives of Biochemistry and Biophysics, 1999, vol. 363, No. 1, pp. 43-54.
Declaration by Anders Dybdal Nielsen dated Sep. 6, 2013 (filed with the Proprietor-Appellant's submissions of Sep. 9, 2013).
Declaration by Janus Krarup dated Dec. 22, 2008 (filed with the Opponent-Appellant's submissions of Sep. 9, 2013).
Declaration by Janus Krarup dated Apr. 22, 2014.
Internal Memo dated Sep. 1, 2007 providing supporting data relating to Declaration of Niels K Klausen signed in 2011.
Presentation by Daniel E Rasmussen & Janus Krarup, originally presented at the 2007 HIC-RPC Conference, Mar. 2007, Interlaken Switzerland.
Summary Report of original experimental data as provided in Declaration of Niels K. Klausen signed in 2011.

\* cited by examiner

SEQUENCE LISTING

```
<160> NUMBER OF SEQ ID NOS: 1

<210> SEQ ID NO 1
<211> LENGTH: 406
<212> TYPE: PRT
<213> ORGANISM: Homo sapiens
<223> OTHER INFORMATION: Human Wild Type Factor FVII

<400> SEQUENCE: 1

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205
```

-continued

```
Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
                260                 265                 270

Leu Ala Phe Val Arg Phe Ser Leu Val Ser Gly Trp Gly Gln Leu Leu
            275                 280                 285

Asp Arg Gly Ala Thr Ala Leu Glu Leu Met Val Leu Asn Val Pro Arg
        290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405
```

O-LINKED GLYCOFORMS OF POLYPEPTIDES AND METHOD TO MANUFACTURE THEM

CROSS-REFERENCE TO RELATED APPLICATIONS

This application is a continuation of U.S. application Ser. No. 11/579,401, filed Jul. 18, 2008 (now abandoned), which is a 35 U.S.C. § 371 National Stage application of International Application PCT/EP2005/052024 (WO 2005/111225), filed May 3, 2005, which claimed priority of Danish Patent Applications PA200400712, filed May 4, 2004, and PA200400882, filed Jun. 4, 2004, and claims the benefit, under 35 U.S.C. § 119(e), of U.S. Provisional Patent Application 60/577,613, filed Jun. 7, 2004; the contents of which are incorporated herein by reference.

In accordance with 37 C.F.R. § 1.52(e)(5), Applicants enclose herewith the Sequence Listing for the above-captioned application entitled "SEQUENCE LISTING", created on Sep. 18, 2017. The Sequence Listing is made up of 4 kilobytes, and the information contained in the attached "SEQUENCE LISTING" is identical to the information in the specification as originally filed. No new matter is added.

FIELD OF THE INVENTION

The present invention relates to compositions comprising glycoproteins having altered patterns of O-linked glycosylation, in particular Factor VII, Factor IX and other blood clotting factors.

BACKGROUND OF THE INVENTION

The biological activity of many glycoproteins is highly dependent upon the presence or absence of particular oligosaccharide structures attached to the glycoprotein. The glycosylation pattern of a therapeutic glycoprotein can affect numerous aspects of the therapeutic efficacy, such as, e.g, solubility, resistance to proteolytic attack, thermal inactivation, immunogenicity, half-life, bioactivity, bioavailability, and stability.

Glycosylation is a complex post-transitional modification that is cell dependent. Following translation, proteins are transported into the endoplasmic reticulum (ER), glycosylated and sent to the Golgi for further processing and subsequent targeting and/or secretion. During glycosylation, either N-linked or O-linked glycoproteins are formed.

Serum proteins involved in coagulation or fibrinolysis, including, e.g., Factor VII and Factor IX are proving to be useful therapeutic agents to treat a variety of pathological conditions. Accordingly, there is an increasing need for formulations comprising these proteins that are pharmaceutically acceptable and exhibit a uniform and predetermined clinical efficacy.

Because of the many disadvantages of using human plasma as a source of pharmaceutical products, it is preferred to produce these proteins in recombinant systems. The clotting proteins, however, are subject to a variety of co- and post-translational modifications, including, e.g., asparagine-linked (N-linked) glycosylation; serine- or threonine-linked (O-linked) glycosylation; and γ-carboxylation of glu residues. These modifications may be qualitatively or quantitatively different when heterologous cells are used as hosts for large-scale production of the proteins. In particular, production in heterologous cells often results in a different array of glycoforms, which identical polypeptides are having different covalently linked oligosaccharide structures.

In different systems, variations in the oligosaccharide structure of therapeutic proteins have been linked to, inter alia, changes in immunogenicity and in vivo clearance. Thus, there is a need in the art for compositions and methods that provide glycoprotein preparations, particularly preparations comprising recombinant Factor IX or recombinant human Factor VII or modified Factor VII or Factor VII-related polypeptides that contain predetermined glycoform patterns.

SUMMARY OF THE INVENTION

The present invention relates to preparations comprising polypeptides that exhibit predetermined serine or threonine-linked glycoform patterns. The preparations are at least about 80% homogenous in respect of the attached glycans or oligosaccharide chains, preferably at least about 90%, at least about 95%, or at least about 98% homologous.

As used herein, a glycoform pattern refers to the distribution within the preparation of oligosaccharide chains having varying structures that are covalently linked to a serine or threonine residue located in an EGF-like domain in the amino acid backbone of the polypeptide.

In one aspect, the invention provides a preparation of a glycoprotein containing a Cys-X1-Ser/Thr-X2-Pro-Cys motif and wherein said serine/threonine forms part of a Glc-O-Ser/Thr covalent bond, said preparation containing a substantially uniform serine/threonine-linked glycosylation pattern.

In one embodiment of the invention, the glycosylation pattern is at least 80% uniform, preferably at least 85%, at least 90%, at least 95%, or at least 98% uniform.

In one embodiment, the serine/threonine-linked glycans are Xyl-Xyl-Glc-; in another, the glycans are Xyl-Glc-; in yet another, the glycans are Glc-.

In different embodiments the glycoproteins are selected from the group of: Factor VII polypeptides, Factor VII-related polypeptides, Factor IX polypeptides, Factor X polypeptides, Factor XII polypeptides, and protein Z polypeptides. In a preferred embodiment, the glycoprotein is selected from the group of: Human Factor VII, Factor VII sequence variants, human Factor IX, and Factor IX sequence variants. In one embodiment, the glycoprotein is a Factor VII variant wherein the ratio between the activity of the Factor VII-variant and the activity of native human factor VIIa (wild-type FVIIa) is at least about 1.25 when tested in the "In Vitro Hydrolysis Assay" as described in the present description, preferably at least about 2.0, or at least about 4.0.

In another aspect the invention provides methods for making preparations of glycoproteins containing Cys-X1-Ser/Thr-X2-Pro-Cys motifs and wherein said serine/threonine forms part of a Glc-O-Ser/Thr covalent bond, said preparations containing a substantially uniform serine/threonine-linked glycosylation pattern. The methods are useful for remodelling or altering the glycosylation pattern present on a glycoprotein upon its initial expression.

More particular, the present invention provide a general enzymatic methodology for the modification of glycans (in particular O-linked glycans) of glycoproteins, in order to improve or enhance their pharmaceutically properties. One method involves treatment of the glycoprotein with xylosidases in order to remove any terminal xylose residues; other methods includes attachment of xylose residues to the exposed glucose or xylose residues on the glycoprotein by treatment with xylosyltransferases; a third method includes attachment of glucose residues to serine and/or threonine amino acid residues in the polypeptide backbone thereby creating a glycosylated polypeptide.

DETAILED DESCRIPTION

Figure 1:
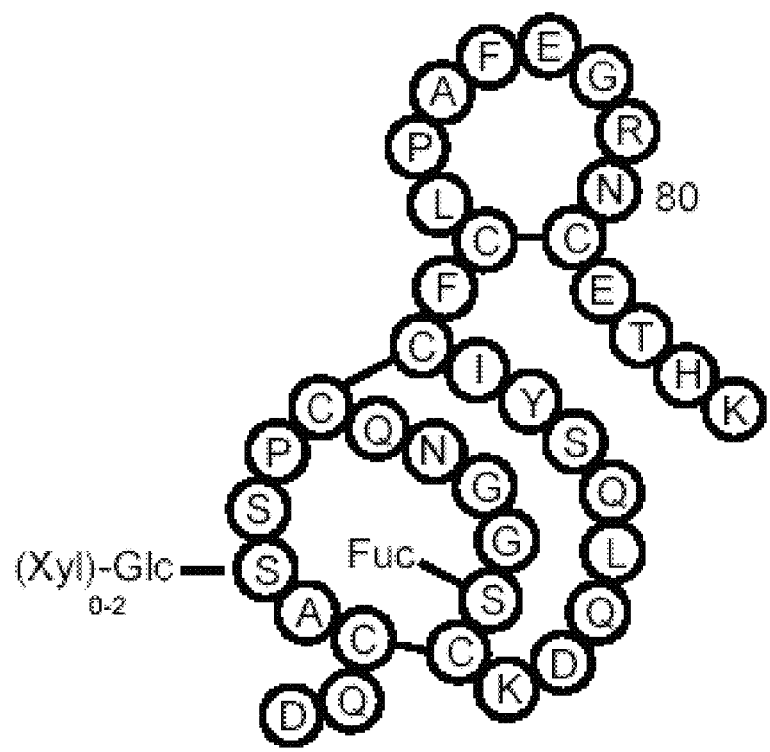
FIG. 1 shows the serine 52 glycosylation of wt-Factor VII.

The following abbreviations are used herein:
Glc=glucosyl
Xyl=xylosyl
Ser=serine (one letter code: S)
Thr=threonine (one letter code: T)
Pro=proline (one letter code: P)
Cys=cysteine (one letter code: C)
FVII=Factor VII
FVIIa=activated (two-chain) Factor VII
FIX=Factor IX
FIXa=activated (two-chain) Factor IX As used herein, a "glycoform pattern" (or "glycosylation pattern") refers to the distribution within the preparation of oligosaccharide chains having varying structures that are covalently linked to a serine or threonine residue located in the amino acid backbone of the polypeptide.

"Homogeneity" refers to the structural consistency across a population of polypeptides with conjugated glycans. Thus, a glycoprotein preparation is said to be about 100% homologous if all contained glycoprotein molecules contain identical glycans attached to the relevant glycosylation site. For example, a preparation of Factor VII polypeptides is said to be at least 90% homologous if at least 90% of the Factor VII polypeptide molecules contain the glycan of interest attached to serine 52 (e.g., Xyl-Xyl-Glc-O-Ser52).

"Substantially uniform glycoform" or "substantially uniform glycosylation" or "substantially uniform glycosylation pattern", when referring to a glycopeptide species, refers to the percentage of acceptor moieties, i.e., serine or threonine residues, that are glycosylated by the glycan of interest. For example, in the case of Factor VII, a substantially uniform glycosylation patterns exists if substantially all (as defined below) of the serine residues in position 52 are glycosylated with the glycan of interest. It is understood by one skilled in the art that the starting material may contain glycosylated serine and/or threonine residues that are glycosylated with a species having the same structure as the glycan of interest. Thus, the calculated percent glycosylation includes serine/threonine residues that are glycosylated with the glycan of interest according to the invention, as well as those serine/threonine residues already glycosylated with the glycan of interest in the starting material.

The term "substantially" is intended to mean that at least about 80%, such as at least about 90%, at least about 95%, or at least about 98% of the serine/threonine residues in the glycoprotein is glycosylated with a predetermined, specific glycan or glycan of interest. The glycosylation pattern is typically determined by one or more methods known to those skilled in the art, such as, e.g., tryptic digestion followed by high performance liquid chromatography (HPLC), liquid-chromatography-mass spectrometry (LC-MS), matrix assisted laser desorption mass time of flight spectrometry (MALDITOF), capillary electrophoresis, and the like.

The term "acceptor moiety" is intended to encompass the group or moiety to which a desired oligo- or mono-saccharide group is transferred such as, without limitation, the serine/threonine residue located within a Cys-X1-Ser/Thr-X2-Pro-Cys motif, a Glc-residue covalently linked to such a serine/threonine residue, or a Xyl-residue covalently linked to a Glc-residue or a Xyl-residue in a Glc-O-Ser/Thr or Xyl-Glc-O-Ser/Thr moiety, respectively.

The term "saccharide donor moiety" is intended to encompass an activated saccharide donor molecule (e.g., a desired oligo- or mono-saccharide structure such as, for example, a xylosyl-xylosyl-donor, xylosyl-donor, or glycosyl-donor) having a leaving group (e.g., xylose-UDP or glucose-UDP) suitable for the donor moiety acting as a substrate for the relevant catalysing enzyme (e.g. glycosyltransferase, xylosidase or xylosyltransferase).

Oligosaccharides are considered to have a reducing and a non-reducing end, whether or not the saccharide at the reducing end is in fact a reducing sugar. In accordance with accepted nomenclature, oligosaccharides are depicted herein with the non-reducing end on the left and the reducing end on the right (e.g., Xyl-Xyl-Glc-O-Ser)

EGF Domain-Containing Polypeptides

The term "EGF domain-containing polypeptides" is intended to encompass peptides, oligopeptides and polypeptides containing one or more epidermal growth factor (EGF)-like domain(s). EGF domains or repeats are small motifs with about 40 amino acids defined by 6 conserved cysteines forming three disulfide bonds. EGF domain-containing polypeptides all contain a consensus sequence for O-glucose modification: Cys1-X1-Ser/Thr-X2-Pro-Cys2 (i.e., a Cys1-X1-Ser-X2-Pro-Cys2 or a Cys1-X1-Thr-X2-Pro-Cys2 consensus sequence) where Cys1 and Cys2 are the first and second conserved cysteines of the EGF repeat and X1 and X2 independently is any amino acid.

The term "glycoprotein" is intended to encompass EGF domain-containing polypeptides containing one or more glycans attached to one or more serine/threonine amino acid residues of the EGF-domain located in the back bone amino acid sequence of the polypeptide.

As used herein, the term "glycan" or, interchangeable, "sugar chain", "oligosaccharide chain" or "oligosaccharide moiety" refers to the entire oligosaccharide structure that is covalently linked to a single serine/threonine residue. The glycan may comprise one or more saccharide units; examples of glycans include, e.g., Glc-, Xyl-Glc-, and Xyl-Xyl-Glc-.

The term "O-glycosylation site" is intended to indicate the glycosylation site at serine/threonine (i.e., Ser or Thr) located within the motif Cys1-X1-Ser/Thr-X2-Pro-Cys2 where Cys1 and Cys2 are the first and second conserved cysteines of the EGF repeat and X1 and X2 independently is any amino acid. These include the glycosylation site at position Ser-52 (S52) of human wt-FVII and the corresponding residues in homologous polypeptides such as, without limitation, FVII sequence variants and FIX polypeptides. The term "corresponding residues" is intended to indicate the Ser or Thr amino acid residue corresponding to the Ser52 residue of wild-type Factor VII (see FIG. 1) when the sequences are aligned. Amino acid sequence homology/ identity is conveniently determined from aligned sequences, using a suitable computer program for sequence alignment, such as, e.g., the ClustalW program, version 1.8, 1999 (Thompson et al., 1994, Nucleic Acid Research, 22: 4673-4680). For example, the wt-factor VII Ser52-residue corresponds to the Ser53-residue of wt-Factor IX. It is further to be understood that polypeptide variants may be created containing non-naturally occurring Cys-X1-Ser/Thr-X2-Pro-Cys motifs and thereby containing non-naturally occurring O-glycosylation sites that can be glycosylated in accordance with the present invention. In one embodiment of the invention, the O-glycosylation site is a serine-glycosylation site and the motif is Cys1-X1-Ser-X2-Pro-Cys2. In another embodiment, the O-glycosylation site is a threonine-glycosylation site and the motif is Cys1-X1-Thr-X2-Pro-Cys2.

The term "terminal glucose" is intended to encompass glucose residues linked as the terminal sugar residue in a glycan, or oligosaccharide chain, i.e., the terminal sugar of each antenna is glucose. The term "terminal xylose" is intended to encompass xylose residues linked as the terminal sugar residue in a glycan, or oligosaccharide chain.

Enzymes

Protein O-glycosyltransferase may be prepared as described, e.g., in Shao et al. (*Glycobiology* 12(11): 763-770 (2002)).

The alpha-xylosidase enzymes may be prepared, e.g., as described by Monroe et al. (*Plant Physiology and Biochemistry* 41:877-885 (2003)).

The enzyme, UDP-D-xylose: β-D-glucoside α-1,3-D-xylosyltransferase can be prepared from HepG2 cells as described by Omichi et al. (*Eur. J. Biochem.* 245:143-146 (1997)).

The enzyme, UDP-D-xylose: α-D-xyloside α1,3-xylosyltransferase can be prepared from HepG2 cells as described by Minamida et al. ((*J. Biochem.* (Tokyo) 120: 1002-1006 (1996)).

UDP-beta-D-glucose is commercially available from, e.g., Sigma (Sigma U4625)

UDP-D-xylose is commercially available from, e.g., Sigma (Sigma U5875)

Glycoproteins

The motif: Cys-X1-Ser/Thr-X2-Pro-Cys appears to be primarily found in epidermal growth factor (EGF) domains of multi-modular proteins such as coagulation and fibrinolytic factors. The motif is a consensus sequence for O-glucose modification whereby a serine-glucose (Glc-O-Ser) or threonine-glucose (Glc-O-Thr) bond is formed. Coagulation factors VII, IX, X and XII as well as plasma Protein Z, Fibrillin and thrombospondin have all been shown to contain the Cys-X1-Ser/Thr-X2-Pro-Cys consensus sequence. Of these, Factors VII and IX and Protein Z have been described to contain the consensus sequence Cys-X1-Ser-X2-Pro-Cys.

The thrombospondins are a family of extracellular proteins that participate in cell-to-cell and cell-to-matrix communication. The proteins are secreted from platelets. They regulate cellular phenotype during tissue genesis and repair.

Protein Z is a vitamin k-dependent plasma protein whose structure is similar to that of Factors VII, IX and X. In contrast to these proteins, however, Protein Z is not the zymogen of a serine protease because it lacks the His and Ser residues of the catalytic triad. Like Proteins C and S, Protein Z participates in limiting the coagulation response, believably by assisting in inhibition of activated Factor X (FXa).

Factor X (Stuart Prower Factor) is a vitamin K-dependent serine protease which participates in the blood clotting process by participating in activation of prothrombin into thrombin.

Factor XII (Hageman factor) is a blood coagulation factor activated by contact with the sub-endothelial surface of an injured vessel. Along with prekallikrein, it serves as the contact factor that initiates the intrinsic pathway of blood coagulation. Kallikrein activates factor XII to XIIa.

Factor IX (Christmas factor) is a vitamin K-dependent serine protease which participates in the blood clotting process by participating in activation of FX into FXa.

Factor VII (proconvertin) is a vitamin K-dependent serine protease which participates in the blood clotting process by participating in activation of prothrombin into thrombin. FVII is activated into FVIIa by contact with exposed tissue factor (TF) at sites of injury of the vessel wall.

Factor VII Polypeptides and Factor VII-Related Polypeptides

As used herein, the terms "Factor VII polypeptide" or "FVII polypeptide" means any protein comprising the amino acid sequence 1-406 of wild-type human Factor VIIa (i.e., a polypeptide having the amino acid sequence disclosed in U.S. Pat. No. 4,784,950), variants thereof as well as Factor VII-related polypeptides, Factor VII derivatives and Factor VII conjugates. This includes FVII variants, Factor VII-related polypeptides, Factor VII derivatives and Factor VII conjugates exhibiting substantially the same or improved biological activity relative to wild-type human Factor VIIa.

The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa. Such variants of Factor VII may exhibit different properties relative to human Factor VII, including stability, phospholipid binding, altered specific activity, and the like.

As used herein, "wild type human FVIIa" is a polypeptide having the amino acid sequence disclosed in U.S. Pat. No. 4,784,950.

As used herein, "Factor VII-related polypeptides" encompasses polypeptides, including variants, in which the Factor VIIa biological activity has been substantially modified, such as reduced, relative to the activity of wild-type Factor VIIa. These polypeptides include, without limitation, Factor VII or Factor VIIa into which specific amino acid sequence alterations have been introduced that modify or disrupt the bioactivity of the polypeptide.

The term "Factor VII derivative" as used herein, is intended to designate a FVII polypeptide exhibiting substantially the same or improved biological activity relative to wild-type Factor VII, in which one or more of the amino acids of the parent peptide have been genetically and/or chemically and/or enzymatically modified, e.g. by alkylation, glycosylation, PEGylation, acylation, ester formation or amide formation or the like. This includes but is not limited to PEGylated human Factor VIIa, cysteine-PEGylated human Factor VIIa and variants thereof. Non-limiting examples of Factor VII derivatives includes GlycoPegylated FVII derivatives as disclosed in WO 03/31464 and US Patent applications US 20040043446, US 20040063911, US 20040142856, US 20040137557, and US 20040132640 (Neose Technologies, Inc.); FVII conjugates as disclosed in WO 01/04287, US patent application 20030165996, WO 01/58935, WO 03/93465 (Maxygen ApS) and WO 02/02764, US patent application 20030211094 (University of Minnesota).

The term "improved biological activity" refers to FVII polypeptides with i) substantially the same or increased proteolytic activity compared to recombinant wild type human Factor VIIa or ii) to FVII polypeptides with substantially the same or increased TF binding activity compared to recombinant wild type human Factor VIIa or iii) to FVII polypeptides with substantially the same or increased half life in blood plasma compared to recombinant wild type human Factor VIIa. The term "PEGylated human Factor VIIa" means human Factor VIIa, having a PEG molecule conjugated to a human Factor VIIa polypeptide. It is to be understood, that the PEG molecule may be attached to any part of the Factor VIIa polypeptide including any amino acid residue or carbohydrate moiety of the Factor VIIa polypeptide. The term "cysteine-PEGylated human Factor VIIa" means Factor VIIa having a PEG molecule conjugated to a sulfhydryl group of a cysteine introduced in human Factor VIIa.

Non-limiting examples of Factor VII variants having substantially the same or increased proteolytic activity compared to recombinant wild type human Factor VIIa include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Komfelt et al., Arch. Biochem. Biophys. 363:43-54, 1999); FVII variants as disclosed in PCT/DK02/00189 (corresponding to WO 02/077218); and FVII variants exhibiting increased proteolytic stability as disclosed in WO 02/38162 (Scripps Research Institute); FVII variants having a modified Gla-domain and exhibiting an enhanced membrane binding as disclosed in WO 99/20767, US patents U.S. Pat. Nos. 6,017,882 and 6,747,003, US patent application 20030100506 (University of Minnesota) and WO 00/66753, US patent applications US 20010018414, US 2004220106, and US 200131005, US patents U.S. Pat. Nos. 6,762,286 and 6,693,075 (University of Minnesota); and FVII variants as disclosed in WO 01/58935, US patent U.S. Pat. No. 6,806, 063, US patent application 20030096338 (Maxygen ApS), WO 03/93465 (Maxygen ApS), WO 04/029091 (Maxygen ApS), WO 04/083361 (Maxygen ApS), and WO 04/111242 (Maxygen ApS), as well as in WO 04/108763 (Canadian Blood Services).

Non-limiting examples of FVII variants having increased biological activity compared to wild-type FVIIa include FVII variants as disclosed in WO 01/83725, WO 02/22776, WO 02/077218, PCT/DK02/00635 (corresponding to WO 03/027147), Danish patent application PA 2002 01423 (corresponding to WO 04/029090), Danish patent application PA 2001 01627 (corresponding to WO 03/027147); WO 02/38162 (Scripps Research Institute); and FVIIa variants with enhanced activity as disclosed in JP 2001061479 (Chemo-Sero-Therapeutic Res Inst.).

Examples of variants of factor VII include, without limitation, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158T/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/ K337A/E296V-FVII, K316Q/L305V/K337A/V158D-FVII, K316Q/L305V/V158D/M298Q-FVII, K316Q/L305V/ V158D/E296V-FVII, K316Q/L305V/V158T/M298Q-FVII, K316Q/L305V/V158T/E296V-FVII, K316Q/L305V/ E296V/M298Q-FVII, K316Q/L305V/V158D/E296V/ M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/ L305V/V158D/K337A/M298Q-FVII, K316Q/L305V/ V158D/E296V/K337A-FVII, K316Q/L305V/V158D/ E296V/M298Q/K337A-FVII, K316Q/L305V/V158T/ E296V/M298Q/K337A-FVII, F374Y/K337A-FVII, F374Y/ V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/ K337A/E296V-FVII, F374Y/L305V/K337A/M298Q-FVII, F374Y/L305V/K337A/V158T-FVII, F374Y/L305V/ K337A/S314E-FVII, F374Y/L305V/V158D/E296V-FVII, F374Y/L305V/V158D/M298Q-FVII, F374Y/L305V/ V158D/S314E-FVII, F374Y/L305V/E296V/M298Q-FVII, F374Y/L305V/E296V/V158T-FVII, F374Y/L305V/ E296V/S314E-FVII, F374Y/L305V/M298Q/V158T-FVII, F374Y/L305V/M298Q/S314E-FVII, F374Y/L305V/ V158T/S314E-FVII, F374Y/K337A/S314E/V158T-FVII, F374Y/K337A/S314E/M298Q-FVII, F374Y/K337A/ S314E/E296V-FVII, F374Y/K337A/S314E/V158D-FVII, F374Y/K337A/V158T/M298Q-FVII, F374Y/K337A/ V158T/E296V-FVII, F374Y/K337A/M298Q/E296V-FVII, F374Y/K337A/M298Q/V158D-FVII, F374Y/K337A/ E296V/V158D-FVII, F374Y/V158D/S314E/M298Q-FVII, F374Y/V158D/S314E/E296V-FVII, F374Y/V158D/ M298Q/E296V-FVII, F374Y/V158T/S314E/E296V-FVII, F374Y/V158T/S314E/M298Q-FVII, F374Y/V158T/ M298Q/E296V-FVII, F374Y/E296V/S314E/M298Q-FVII, F374Y/L305V/M298Q/K337A/S314E-FVII, F374Y/ L305V/E296V/K337A/S314E-FVII, F374Y/E296V/ M298Q/K337A/S314E-FVII, F374Y/L305V/E296V/ M298Q/K337A-FVII, F374Y/L305V/E296V/M298Q/ S314E-FVII, F374Y/V158D/E296V/M298Q/K337A-FVII, F374Y/V158D/E296V/M298Q/S314E-FVII, F374Y/ L305V/V158D/K337A/S314E-FVII, F374Y/V158D/ M298Q/K337A/S314E-FVII, F374Y/V158D/E296V/ K337A/S314E-FVII, F374Y/L305V/V158D/E296V/ M298Q-FVII, F374Y/L305V/V158D/M298Q/K337A-FVII, F374Y/L305V/V158D/E296V/K337A-FVII, F374Y/ L305V/V158D/M298Q/S314E-FVII, F374Y/L305V/ V158D/E296V/S314E-FVII, F374Y/V158T/E296V/ M298Q/K337A-FVII, F374Y/V158T/E296V/M298Q/ S314E-FVII, F374Y/L305V/V158T/K337A/S314E-FVII, F374Y/V158T/M298Q/K337A/S314E-FVII, F374Y/ V158T/E296V/K337A/S314E-FVII, F374Y/L305V/ V158T/E296V/M298Q-FVII, F374Y/L305V/V158T/ M298Q/K337A-FVII, F374Y/L305V/V158T/E296V/ K337A-FVII, F374Y/L305V/V158T/M298Q/S314E-FVII, F374Y/L305V/V158T/E296V/S314E-FVII, F374Y/E296V/ M298Q/K337A/V158T/S314E-FVII, F374Y/V158D/
E296V/M298Q/K337A/S314E-FVII, V158D/E296V/M298Q/S314E-FVII, E296V/M298Q/V158T/S314E-FVII, E296V/M298Q/K337A/V158T-FVII, E296V/K337A/V158T/S314E-FVII, M298Q/K337A/V158T/S314E-FVII, V158D/E296V/M298Q/K337A-FVII, V158D/E296V/K337A/S314E-FVII, V158D/M298Q/K337A/S314E-FVII, F374Y/L305V/ F374Y/L305V/ F374Y/L305V/ F374Y/L305V/ F374Y/L305V/ F374Y/L305V/ F374Y/L305V/ F374Y/L305V/ F374Y/L305V/ E296V/M298Q/K337A/V158T/S314E-FVII, F374Y/ L305V/V158D/E296V/M298Q/K337A/S314E-FVII, S52A-Factor VII, S60A-Factor VII; R152E-Factor VII, S344A-Factor VII, T106N-FVII, K143N/N145T-FVII, V253N-FVII, R290N/A292T-FVII, G291N-FVII, R315N/ V317T-FVII, K143N/N145T/R315N/V317T-FVII; and FVII having substitutions, additions or deletions in the amino acid sequence from 233Thr to 240Asn; FVII having substitutions, additions or deletions in the amino acid sequence from 304Arg to 329Cys; and FVII having substitutions, additions or deletions in the amino acid sequence from 153Ile to 223Arg.

Factor VII variants having substantially the same or improved biological activity relative to wild-type Factor VIIa encompass those that exhibit at least about 25%, such as, e.g., at least about 50%, at least about 75%, at least about 90%, at least about 120, at least about 130, or at least about 150% of the specific activity of wild-type Factor VIIa that has been produced in the same cell type, when tested in one or more of a clotting assay, proteolysis assay, or TF binding assay as described above. Factor VII variants having substantially reduced biological activity relative to wild-type Factor VIIa are those that exhibit less than about 25%, preferably less than about 10%, more preferably less than about 5% and most preferably less than about 1% of the specific activity of wild-type Factor VIIa that has been produced in the same cell type when tested in one or more of a clotting assay, proteolysis assay, or TF binding assay as described below. Factor VII variants having a substantially modified biological activity relative to wild-type Factor VII include, without limitation, Factor VII variants that exhibit TF-independent Factor X proteolytic activity and those that bind TF but do not cleave Factor X.

The biological activity of Factor VIIa in blood clotting derives from its ability to (i) bind to tissue factor (TF) and (ii) catalyze the proteolytic cleavage of Factor IX or Factor X to produce activated Factor IX or X (Factor IXa or Xa, respectively). For purposes of the invention, Factor VIIa biological activity may be quantified by measuring the ability of a preparation to promote blood clotting using Factor VII-deficient plasma and thromboplastin, as described, e.g., in U.S. Pat. No. 5,997,864. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by (i) measuring the ability of Factor VIIa to produce of Factor Xa in a system comprising TF embedded in a lipid membrane and Factor X. (Persson et al., J. Biol. Chem. 272: 19919-19924, 1997); (ii) measuring Factor X hydrolysis in an aqueous system (see, "General Methods" below); (iii) measuring its physical binding to TF using an instrument based on surface plasmon resonance (Persson, FEBS Lefts. 413:359-363, 1997) (iv) measuring hydrolysis of a synthetic substrate (see, "General Methods" below); and (v) measuring generation of thrombin in a TF-independent in vitro system (see, "General Methods" below).

Factor IX Polypeptides and Factor IX-Related Polypeptides

The present invention encompasses factor IX polypeptides, such as, e.g., those having the amino acid sequence disclosed in, e.g., Jaye et al., Nucleic Acids Res. 11: 2325-2335, 1983. (wild-type human factor IX).

In practicing the present invention, any factor IX polypeptide may be used that is effective in preventing or treating bleeding. This includes factor IX polypeptides derived from blood or plasma, or produced by recombinant means.

As used herein, "factor IX polypeptide" encompasses, without limitation, factor IX, as well as factor IX-related polypeptides. The term "factor IX" is intended to encompass, without limitation, polypeptides having the amino acid sequence as described in Jaye et al., Nucleic Acids Res. 1983 (see above) (wild-type human factor IX), as well as wild-type Factor IX derived from other species, such as, e.g., bovine, porcine, canine, murine, and salmon Factor IX. It further encompasses natural allelic variations of Factor IX that may exist and occur from one individual to another. Also, degree and location of glycosylation or other post-translation modifications may vary depending on the chosen host cells and the nature of the host cellular environment. The term "Factor IX" is also intended to encompass Factor IX polypeptides in their uncleaved (zymogen) form, as well as those that have been proteolytically processed to yield their respective bioactive forms, which may be designated Factor IXa.

"Factor IX-related polypeptides" include, without limitation, factor IX polypeptides that have either been chemically modified relative to human factor IX and/or contain one or more amino acid sequence alterations relative to human factor IX (i.e., factor IX variants), and/or contain truncated amino acid sequences relative to human factor IX (i.e., factor IX fragments). Such factor IX-related polypeptides may exhibit different properties relative to human factor IX, including stability, phospholipid binding, altered specific activity, and the like.

The term "factor IX-related polypeptides" are intended to encompass such polypeptides in their uncleaved (zymogen) form, as well as those that have been proteolytically processed to yield their respective bioactive forms, which may be designated "factor IXa-related polypeptides" or "activated factor IX-related polypeptides".

As used herein, "factor IX-related polypeptides" encompasses, without limitation, polypeptides exhibiting substantially the same or improved biological activity relative to wild-type human factor IX, as well as polypeptides, in which the factor IX biological activity has been substantially modified or reduced relative to the activity of wild-type human factor IX. These polypeptides include, without limitation, factor IX or factor IXa that has been chemically modified and factor IX variants into which specific amino acid sequence alterations have been introduced that modify or disrupt the bioactivity of the polypeptide.

It further encompasses polypeptides with a slightly modified amino acid sequence, for instance, polypeptides having a modified N-terminal end including N-terminal amino acid deletions or additions, and/or polypeptides that have been chemically modified relative to human factor IX.

Factor IX-related polypeptides, including variants of factor IX, whether exhibiting substantially the same or better bioactivity than wild-type factor IX, or, alternatively, exhibiting substantially modified or reduced bioactivity relative to wild-type factor IX, include, without limitation, polypeptides having an amino acid sequence that differs from the sequence of wild-type factor IX by insertion, deletion, or substitution of one or more amino acids.

Factor IX-related polypeptides, including variants, encompass those that exhibit at least about 10%, at least about 20%, at least about 30%, at least about 40%, at least about 50%, at least about 60%, at least about 70%, at least about 80%, at least about 90%, at least about 100%, at least about 110%, at least about 120%, and at least about 130%, of the specific activity of wild-type factor IX that has been produced in the same cell type, when tested in the factor IX activity assay as described in the present specification.

Factor IX-related polypeptides, including variants, having substantially the same or improved biological activity relative to wild-type factor IX encompass those that exhibit at least about 25%, preferably at least about 50%, more preferably at least about 75%, more preferably at least about 100%, more preferably at least about 110%, more preferably at least about 120%, and most preferably at least about 130% of the specific biological activity of wild-type human factor IX that has been produced in the same cell type when tested in one or more of the specific factor IX activity assays as described. For purposes of the invention, factor IX biological activity may be quantified as described later in the present description (see "General Methods").

Factor IX-related polypeptides, including variants, having substantially reduced biological activity relative to wild-type factor IX are those that exhibit less than about 25%, preferably less than about 10%, more preferably less than about 5% and most preferably less than about 1% of the specific activity of wild-type factor IX that has been produced in the same cell type when tested in one or more of the specific factor IX activity assays as described above.

Non-limiting examples of factor IX polypeptides include plasma-derived human factor IX as described, e.g., in Chandra et al., Biochem. Biophys. Acta 1973, 328:456; Andersson et al., Thromb. Res. 1975, 7:451; Suomela et al., Eur. J. Biochem. 1976, 71:145.

Suitable assays for testing for factor IX activity, and thereby providing means for selecting suitable factor IX variants for use in the present invention, can be performed as simple in vitro tests as described, for example, in Wagenvoord et al., Haemostasis 1990; 20(5):276-88. Factor IX biological activity may also be quantified by measuring the ability of a preparation to correct the dotting time of factor IX-deficient plasma, e.g., as described in Nilsson et al., 1959. (Nilsson I M, Blombaeck M, Thilen A, von Francken I., Carriers of haemophilia A—A laboratory study, Acta Med Scan 1959; 165:357). In this assay, biological activity is expressed as units/ml plasma (1 unit corresponds to the amount of FIX present in normal pooled plasma.

In some embodiments of the invention, the factor IX are factor IX-related polypeptides wherein the ratio between the activity of said factor IX polypeptide and the activity of native human factor IX (wild-type factor IX) is at least about 1.25 when tested in the "chromogenic assay" (see below); in other embodiments, the ratio is at least about 2.0; in further embodiments, the ratio is at least about 4.0.

O-Linked Glycosylation

In practicing the present invention, the pattern of oligosaccharides may be determined using any method known in the art, including, without limitation: high-performance liquid chromatography (HPLC); capillary electrophoresis (CE); nuclear magnetic resonance (NMR); mass spectrometry (MS) using ionization techniques such as fast-atom bombardment, electrospray, or matrix-assisted laser desorption (MALDI); gas chromatography (GC); and treatment with exoglycosidases in conjunction with anion-exchange (AIE)-HPLC, size-exclusion chromatography (SEC), or MS. See, e.g., Weber et al., Anal. Biochem. 225:135 (1995);

Klausen et al., J. Chromatog. 718:195 (1995); Morris et al., in Mass Spectrometry of Biological Materials, McEwen et al., eds., Marcel Dekker, (1990), pp 137-167; Conboy et al., Biol. Mass Spectrom. 21:397, 1992; Hellerqvist, Meth. Enzymol. 193:554 (1990); Sutton et al., Anal. Biohcem. 318:34 (1994); Harvey et al., Organic Mass Spectrometry 29:752 (1994).

The relative content of O-glycoforms can be determined, for example, by tryptic peptide mapping. In short, the glycoprotein is digested with trypsin and the polypeptides containing the O-glycosylation site are separated according to the glycan structure by RP-HPLC chromatography, mass spectrometry or another suitable analytical separation technique. If necessary in order to obtaining a suitable separation, the glycoprotein can prior to the digestion with trypsin be reduced and alkylated and the polypeptide chain containing the O-glycosylation site is purified by, e.g. RP-HPLC chromatography. Then the purified polypeptide is subjected to tryptic digestion followed by analysis as described above.

Methods for Producing Glycoprotein Preparations Having a Predetermined Pattern of O-Linked Oligosaccharides The origin of the acceptor glycoprotein is not a critical aspect of the invention. Typically, the glycoprotein will be expressed in a cultured prokaryote cell or eukaryote cell such as a mammalian, yeast insect, fungal or plant cell. The protein, however, may also be isolated from a natural source such as plasma, serum or blood. The glycoprotein can either be a full length protein or a fragment.

The invention provides compositions that include glycoprotein species that have a substantially uniform glycosylation pattern. The methods are useful for remodelling or altering the glycosylation pattern present on a glycoprotein upon its initial expression. Thus, the methods of the invention provide a practical means for large-scale preparation of glycoforms having pre-selected or pre-determined uniform derivatization patterns. The methods are particularly well suited for modification of therapeutic peptides, including but not limited to, glycoproteins that are incompletely glycosylated during production in cell culture cells or transgenic animals. However, the preparations and compositions of the invention may also be prepared by purification of natural sources, such as plasma, serum or blood, or cell culture fluids and isolating the desired glycoforms therefrom.

The polypeptides to be re-modelled in accordance with the invention are typically prepared by cell culture processes. Suitable host cells include, without limitation, human cells expressing an endogenous gene such as, e.g., a Factor VII, IX, X, or XII gene or a protein Z gene. In these cells, the endogenous gene may be intact or may have been modified in situ, or a sequence outside the endogenous gene may have been modified in situ to alter the expression of the endogenous glycoprotein gene. Any human cell capable of expressing an endogenous glycoprotein gene may be used. Other, included host cells are heterologous host cells programmed to express a glycoprotein such as, e.g., human Factor VII or IX or X or XII from a recombinant gene. The host cells may be vertebrate, insect, or fungal cells. Preferably, the cells are mammalian cells capable of the entire spectrum of mammalian N-linked glycosylation; O-linked glycosylation; and γ-carboxylation. See, e.g., U.S. Pat. No. 4,784,950. Preferred mammalian cell lines include the CHO (ATCC CCL 61), COS-1 (ATCC CRL 1650), baby hamster kidney (BHK) and HEK293 (ATCC CRL 1573; Graham et al., J. Gen. Virol. 36:59-72, 1977) cell lines. A preferred BHK cell line is the tk⁻ ts13 BHK cell line (Waechter and Baserga, Proc. Natl. Acad. Sci. USA 79:1106-1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk⁻ ts13 BHK cell line is also available from the ATCC under accession number CRL 1632. In addition, a number of other cell lines may be used, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1) and DUKX cells (CHO cell line) (Urlaub and Chasin, Proc. Natl. Acad. Sci. USA 77:4216-4220, 1980). (DUKX cells also referred to as CXB11 cells), and DG44 (CHO cell line) (Cell, 33:405, 1983, and Somatic Cell and Molecular Genetics 12:555, 1986). Also useful are 3T3 cells, Namalwa cells, myelomas and fusions of myelomas with other cells. Suitable host cells include BHK 21 cells that have been adapted to grow in the absence of serum and have been programmed to express Factor VII. The cells may be mutant or recombinant cells that express a qualitatively or quantitatively different spectrum of glycosylation enzymes (such as, e.g., glycosyl transferases and/or glycosidases) than the cell type from which they were derived. The cells may also be programmed to express other heterologous peptides or proteins, including, e.g., truncated forms of Factor VII. The host cells may also be CHO cells that have been programmed to co-express both the Factor VII polypeptide of interest (i.e., Factor VII or a Factor-VII-related polypeptide) and another heterologous peptide or polypeptide such as, e.g., a modifying enzyme or a Factor VII fragment.

Figure 3:
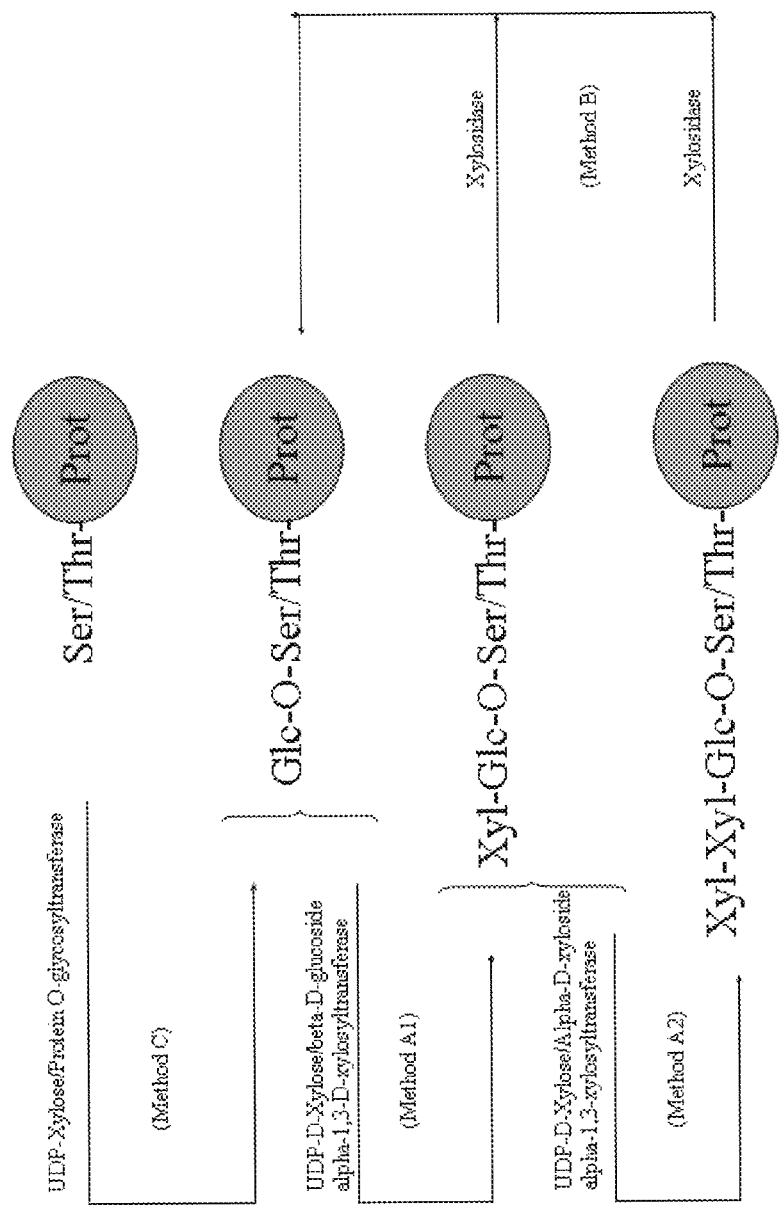
FIG. 3 shows a reaction scheme for the making of a preparation of glycoproteins exhibiting a predetermined serine/threonine-linked glycosylation.

Methods:

The present invention encompasses methods for producing a preparation comprising a predetermined serine/threonine-linked glycoform pattern as described above and, in further embodiments, methods for optimizing the glycoform distribution of a glycoprotein (see FIG. 3). The individual process steps described can be applied in different combinations in order to obtain the desired glycoform pattern. Non-limiting examples are given below.

In one aspect, these methods are carried out by the steps of:

(a) obtaining a preparation of a glycoprotein containing a Cys-X1-Ser/Thr-X2-Pro-Cys motif and wherein said serine/threonine forms part of a Glc-O-Ser/Thr covalent bond from a cell in which it is prepared; e.g., from an engineered cell (cell culture) or by isolating the glycoprotein from a natural source;

(b) contacting the glycoprotein preparation with an activated donor of the desired mono- or oligosaccharide moiety and an enzyme suitable for transferring the desired mono- or oligo-saccharide group under conditions appropriate for transferring the mono- or oligo-saccharide group from the donor moiety to the acceptor moiety, thereby producing the glycopeptide having an altered glycosylation pattern.

In another aspect, these methods are carried out by the steps of:

(aa) obtaining a preparation of a glycoprotein containing a Cys-X1-Ser/Thr-X2-Pro-Cys motif and wherein said serine/threonine forms part of a Glc-O-Ser/Thr covalent bond from a cell in which it is prepared; e.g., from an engineered cell (cell culture) or by isolating the glycoprotein from a natural source;

(bb) contacting the glycoprotein preparation with an enzyme suitable for removing the terminal mono- or oligosaccharide group under conditions appropriate for removing said mono- or oligo-saccharide group, thereby producing the glycopeptide having an altered glycosylation pattern.

In one embodiment, the methods comprise a combination of steps (b) and (bb). In one embodiment the methods further comprise a step of isolating the glycoprotein having an altered glycosylation pattern.

In one embodiment, the methods comprise a further step of:

Analyzing the structure of the oligosaccharides linked to the polypeptides to determine a glycoform pattern, and, optionally, repeating steps (b) and/or (bb) until a desired glycoform pattern is achieved.

These methods may further comprise the step of subjecting preparations having pre-determined glycoform patterns to at least one test of bioactivity (including, e.g., clotting, Factor X proteolysis, or TF binding) or other functionality (such as, e.g., pharmacokinetic profile or stability), and correlating particular glycoform patterns with particular bioactivity or functionality profiles in order to identify a desired glycoform pattern.

In one embodiment, the desired glycoform pattern is a substantially uniform glucose-O-serine/threonine glycosylation: In this embodiment, wherein the initially obtained glycoprotein contains terminal xylose the method (METHOD B) comprises the steps of:

(a) obtaining a preparation of a glycoprotein containing a Cys-X1-Ser/Thr-X2-Pro-Cys motif and wherein said serine/threonine forms part of a Glc-O-Ser/Thr covalent bond from a cell in which it is prepared; e.g., from an engineered cell (cell culture) or by isolating the glycoprotein from a natural source;

(b) contacting the preparation obtained in step (a) with a xylosidase under conditions appropriate for removing xylose residues from the glycoprotein, thereby producing the glycoprotein having an altered glycosylation pattern.

In one embodiment, the method further includes the step of isolating the glycoprotein prepared in step b having a Glc-O-Ser/Thr glycosylation.

In one embodiment, the method further includes the step of analysing the structure of the oligosaccharides linked to the polypeptides to determine a glycoform pattern, and, optionally, repeating step (b) until the desired glycoform pattern is achieved.

In another embodiment for making a desired glycoforms pattern in the form of a substantially uniform glucose-O-serine/threonine glycosylation, the method (METHOD C) comprises the steps of:

(a) obtaining a preparation of a polypeptide containing a Cys-X1-Ser/Thr-X2-Pro-Cys motif, e.g., from an engineered cell (cell culture) or by isolating the glycoprotein from a natural source;

(b) contacting the preparation obtained in step (a) with a O-glucosyltransferase and an activated glucose donor under conditions appropriate for transferring a glucose residue from the glucose donor moiety to the serine/threonine acceptor moiety, thereby producing the polypeptide having an altered glycosylation pattern.

In one embodiment, the method further includes the step of isolating the glycoprotein prepared in step b having a Glc-O-Ser/Thr glycosylation.

In one embodiment, the method further includes the step of analysing the structure of the oligosaccharides linked to the polypeptides to determine a glycoform pattern, and, optionally, repeating step (b) until the desired glycoform pattern is achieved.

In one embodiment, the desired glycoform pattern is a substantially uniform xylose-glucose-O-serine/threonine glycosylation: In this embodiment, the method (METHOD A1) comprises the steps of:

(a) obtaining a preparation of a glycoprotein containing a Cys-X1-Ser/Thr-X2-Pro-Cys motif and wherein said serine/threonine forms part of a Glc-O-Ser/Thr covalent bond; e.g., from an engineered cell (cell culture) or by isolating the glycoprotein from a natural source;

(b) contacting the preparation obtained in step (a) with UDP-D-xylose: β-D-glucoside α-1,3-D-xylosyltransferase and an activated xylosyl donor under conditions appropriate for transferring a xylose residue from the xylose donor moiety to the acceptor moiety, thereby producing the glycopeptide having an altered glycosylation pattern.

In one embodiment, the method further includes the step of isolating the glycoprotein prepared in step b having a Xyl-Glc-O-Ser/Thr glycosylation.

In one embodiment, the method further includes the step of analysing the structure of the oligosaccharides linked to the polypeptides to determine a glycoform pattern, and, optionally, repeating step (b) until the desired glycoform pattern is achieved.

In one embodiment, the method further includes the step of removing terminal xylose-residues by subjecting the preparation obtained in step (a) to METHOD B prior to step (b).

In one embodiment, the desired glycoform pattern is a substantially uniform xylose-xylose-glucose-O-serine/threonine glycosylation: In this embodiment, the method (METHOD A2) comprises the steps of:

(a) obtaining a preparation of a glycoprotein containing a Cys-X1-Ser/Thr-X2-Pro-Cys motif and wherein said serine/threonine forms part of a Glc-O-Ser/Thr covalent bond; e.g., from an engineered cell (cell culture) or by isolating the glycoprotein from a natural source;

(b) contacting the preparation obtained in step (a) with UDP-D-xylose: β-D-glucoside α-1,3-D-xylosyltransferase and an activated xylosyl donor under conditions appropriate for transferring a xylose residue from the xylose donor moiety to the acceptor moiety, thereby producing the glycopeptide having an altered glycosylation pattern.

(c) contacting the preparation obtained in step (b) with UDP-D-xylose: α-D-xyloside α-1,3-xylosyltransferase and an activated xylosyl donor under conditions appropriate for transferring a xylose residue from the xylose donor moiety to the acceptor moiety, thereby producing the glycopeptide having an altered glycosylation pattern.

In one embodiment, the method further includes the step of isolating the preparation obtained in step (b) prior to subjecting the preparation to step (c).

In one embodiment, the method further includes the step of isolating the glycoprotein prepared in step (c) having a Xyl-Xyl-Glc-O-Ser/Thr glycosylation.

In one embodiment, the method further includes the step of analysing the structure of the oligosaccharides linked to the polypeptides to determine a glycoform pattern, and, optionally, repeating step (b) and/or step (c) until the desired glycoform pattern is achieved.

In one embodiment, the method further includes the step of removing terminal xylose-residues by subjecting the preparation obtained in step (a) to METHOD B prior to step (b).

In different embodiments, the glycoprotein exhibits substantially uniform Xyl-Xyl-Glc-O-Ser glycosylation, Xyl-Glc-O-Ser glycosylation, and Glc-O-Ser glycosylation; Ser being the serine of the contained Cys-X1-Ser-X2-Pro-Cys motif (X1 and X2 independently being any amino acid residue). In other, different embodiments, the glycoprotein exhibits substantially uniform Xyl-Xyl-Glc-O-Thr glycosylation, Xyl-Glc-O-Thr glycosylation, and Glc-O-Thr glycosylation; Thr being the threonine of the contained Cys-X1-Thr-X2-Pro-Cys motif (X1 and X2 independently being any amino acid residue).

In different embodiments, the polypeptides are selected from the list of: Factor VII polypeptides, Factor VII-related polypeptides, Factor IX polypeptides, Factor IX-related polypeptides, Factor X polypeptides, and Factor X-related polypeptides.

In preferred embodiments, the glycoprotein preparation is selected from the list of:

Factor VII polypeptides exhibiting substantially uniform Xyl-Xyl-Glc-O-Ser52 glycosylation, Factor VII polypeptides exhibiting substantially uniform Xyl-Glc-O-Ser52 glycosylation Factor VII polypeptides exhibiting substantially uniform Glc-O-Ser52 glycosylation Factor VII-related polypeptides exhibiting substantially uniform Xyl-Xyl-Glc-O-Ser52 glycosylation Factor VII-related polypeptides exhibiting substantially uniform Xyl-Glc-O-Ser52 glycosylation Factor VII-related polypeptides exhibiting substantially uniform Glc-O-Ser52 glycosylation Factor VII variants exhibiting substantially uniform Xyl-Xyl-Glc-O-Ser52 glycosylation Factor VII variants exhibiting substantially uniform Xyl-Glc-O-Ser52 glycosylation Factor VII variants exhibiting substantially uniform Glc-O-Ser52 glycosylation Factor IX polypeptides exhibiting substantially uniform Xyl-Xyl-Glc-O-Ser53 glycosylation Factor IX polypeptides exhibiting substantially uniform Xyl-Glc-O-Ser53 glycosylation Factor IX polypeptides exhibiting substantially uniform Glc-O-Ser53 glycosylation Factor IX-related polypeptides exhibiting substantially uniform Xyl-Xyl-Glc-O-Ser53 glycosylation Factor IX-related polypeptides exhibiting substantially uniform Xyl-Glc-O-Ser53 glycosylation Factor IX-related polypeptides exhibiting substantially uniform Glc-O-Ser53 glycosylation Factor IX variants exhibiting substantially uniform Xyl-Xyl-Glc-O-Ser53 glycosylation Factor IX variants exhibiting substantially uniform Xyl-Glc-O-Ser53 glycosylation Factor IX variants exhibiting substantially uniform Glc-O-Ser53 glycosylation It is to be understood that oligosaccharides such as Xyl-Xyl- may also be transferred to the acceptor Glc-O-Ser/Thr moiety by using a suitable transferring enzyme and an activated Xyl-Xyl- donor.

Chromatographic Method:

The present invention also encompasses hydrophobic interaction chromatographic methods for producing a preparation comprising a predetermined serine/threonine-linked glycoform pattern as described above, and for purifying a O-glycosylated polypeptide having a desired glycoform pattern from a composition comprising said polypeptide and polypeptides having unwanted glycoform patterns.

In one aspect, the method comprises the following steps:

(a) obtaining a preparation of a glycoprotein containing a Cys-X1-Ser/Thr-X2-Pro-Cys motif and wherein said serine/threonine forms part of a Glc-O-Ser/Thr covalent bond from a cell in which it is prepared; e.g., from an engineered cell (cell culture) or by isolating the glycoprotein from a natural source;

(b) binding the glycoprotein to an hydrophic interaction material using a solution comprising water, optionally a salt component, and optionally a buffer;

(c) optionally washing the hydrophobic interaction material using a solution comprising water, optionally a salt component, and optionally a buffer so as to elute contaminants from the hydrophobic interaction material;

(d) washing the hydrophobic interaction material using a solution comprising an organic modifier, water, optionally a salt component, and optionally a buffer, at a linear or step gradient or isocratically in salt component so as to separate glycoproteins having a desired glycoform patter from glycoproteins not having the desired glycoform from the hydrophobic interaction material;

(e) collecting the fraction containing the glycoproteins having the desired glycoform pattern.

In one embodiment, the above-described methods further includes the step of repeating steps (a) to e) by subjecting the preparation obtained in step (e) to steps (a) to (e). This further step may be repeated more than once if deemed necessary.

It is to be understood that the preparations according to the invention may also be prepared by a process comprising a combination of purification steps whereby glycoprotein species having the desired glycosylation are captured from the cell culture liquid or natural source of origin and the above-described enzymatic methods.

The above-described methods may further comprise the step of subjecting preparations having predetermined glycoform patterns to at least one test of bioactivity (including, e.g., clotting, Factor X proteolysis, or TF binding) or other functionality (such as, e.g., pharmacokinetic profile or stability), and correlating particular glycoform patterns with particular bioactivity or functionality profiles in order to identify a desired glycoform pattern.

Further enzymatic treatments may be used in connection with the above methods to modify the oligosaccharide pattern of N- or O-linked glycans of a preparation; such treatments include, without limitation, treatment with one or more of sialidase (neuraminidase), galactosidase, fucosidase; galactosyl transferase, fucosyl transferase, and/or sialyltransferase, in a sequence and under conditions that achieve a desired modification in the distribution of oligosaccharide chains having particular terminal structures. Glycosyl transferases are commercially available from Calbiochem (La Jolla, Calif.) and glycosidases are commercially available from Glyko, Inc., (Novato, Calif.).

Glycoprotein Preparations

As used herein, a "glycoprotein preparation" refers to a plurality of glycoforms that have been separated from the cell in which they were synthesized. The glycoprotein preparation include inactivated forms, activated forms, functionally related polypeptides such as, e.g., variants and chemically modified forms, that have been separated from the cell in which they were synthesized.

For example, as used herein, a "Factor VII preparation" refers to a plurality of Factor VII polypeptides, Factor VIIa polypeptides, or Factor VII-related polypeptides, including variants and chemically modified forms, that have been separated from the cell in which they were synthesized or isolated from a natural source. Likewise, a "Factor IX preparation" refers to a plurality of Factor IX polypeptides, Factor IXa polypeptides, or Factor IX-related polypeptides, including variants or chemically modified forms, that have been separated from the cell in which they were synthesized or isolated from a natural source (e.g., plasma, serum, blood).

Separation of polypeptides from their cell of origin may be achieved by any method known in the art, including, without limitation, removal of cell culture medium containing the desired product from an adherent cell culture; centrifugation or filtration to remove non-adherent cells; and the like.

Optionally, the polypeptides may be further purified. Purification may be achieved using any method known in the art, including, without limitation, affinity chromatography, such as, e.g., on an anti-Factor VII or anti-Factor IX antibody column (see, e.g., Wakabayashi et al., *J. Biol. Chem.* 261:11097, 1986; and Thim et al., *Biochem.* 27:7785, 1988); hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, *Protein Purification*, Springer-Verlag, New York, 1982; and *Protein Purification*, J. C. Janson and Lars Ryden, editors, VCH Publishers, New York, 1989. Following purification, the preparation preferably contains less than about 10% by weight, more preferably less than about 5% and most preferably less than about 1%, of non-related proteins derived from the host cell.

Factor VII and Factor VII-related polypeptides, Factor IX and Factor IX-related polypeptides, or Factor X and Factor X-related polypeptides, respectively, may be activated by proteolytic cleavage, using Factor XIIa or other proteases having trypsin-like specificity, such as, e.g., Factor IXa, kallikrein, Factor Xa, and thrombin. See, e.g., Osterud et al., *Biochem.* 11:2853 (1972); Thomas, U.S. Pat. No. 4,456,591; and Hedner et al., *J. Clin. Invest.* 71:1836 (1983). Alternatively, Factor VII, IX or X, respectively, may be activated by passing it through an ion-exchange chromatography column, such as Mono Q® (Pharmacia) or the like. The resulting activated polypeptide, e.g., Factor VII, may then be formulated and administered as described below.

Functional Properties of Glycoprotein Preparations

The preparations of glycoproteins having predetermined oligosaccharide patterns according to the invention (including Factor VII polypeptides, Factor VII-related polypeptides, Factor IX polypeptides and Factor IX-related polypeptides) exhibit improved functional properties relative to reference preparations. The improved functional properties may include, without limitation, a) physical properties such as, e.g., storage stability; b) pharmacokinetic properties such as, e.g., bioavailability and half-life; c) immunogenicity in humans, and d) biological activity, such as, e.g., clotting activity.

A reference preparation refers to a preparation comprising a polypeptide that is identical to that contained in the preparation of the invention to which it is being compared (such as, e.g., wild-type Factor VII or wild-type Factor IX or a particular variant or chemically modified form) except for exhibiting a different pattern of serine/threonine-linked glycosylation.

Storage stability of a glycoprotein (e.g., Factor VII) preparation may be assessed by measuring (a) the time required for 20% of the bioactivity of a preparation to decay when stored as a dry powder at 25° C. and/or (b) the time required for a doubling in the proportion of (e.g., Factor VIIa) aggregates of said glycoprotein in the preparation.

In some embodiments, the preparations of the invention exhibit an increase of at least about 30%, preferably at least about 60% and more preferably at least about 100%, in the time required for 20% of the bioactivity to decay relative to the time required for the same phenomenon in a reference preparation, when both preparations are stored as dry powders at 25° C. Bioactivity measurements may be performed using any of a clotting assay, proteolysis assay, TF-binding assay, or TF-independent thrombin generation assay.

In some embodiments, the preparations of the invention exhibit an increase of at least about 30%, preferably at least about 60%, and more preferably at least about 100%, in the time required for doubling of aggregates relative to a reference preparation, when both preparations are stored as dry powders at 25° C. The contents of aggregates may be determined according to methods known to the skilled person, such as, e.g., gel permeation HPLC methods. For example, the content of Factor VII aggregates is determined by gel permeation HPLC on a Protein Pak 300 SW column (7.5×300 mm) (Waters, 80013) as follows. The column is equilibrated with Eluent A (0.2 M ammonium sulfate, 5% isopropanol, pH adjusted to 2.5 with phosphoric acid, and thereafter pH is adjusted to 7.0 with triethylamine), after which 25 µg of sample is applied to the column. Elution is with Eluent A at a flow rate of 0.5 ml/min for 30 min, and detection is achieved by measuring absorbance at 215 nm. The content of aggregates is calculated as the peak area of the Factor VII aggregates/total area of Factor VII peaks (monomer and aggregates).

"Bioavailability" refers to the proportion of an administered dose of a (e.g., Factor VII or Factor VII-related) glycoprotein preparation that can be detected in plasma at predetermined times after administration. Typically, bioavailability is measured in test animals by administering a dose of between about 25-250 µg/kg of the preparation; obtaining plasma samples at predetermined times after administration; and determining the content of (e.g., Factor VII or Factor VII-related) glycosylated polypeptides in the samples using one or more of a clotting assay (or any bioassay), an immunoassay, or an equivalent. The data are typically displayed graphically as polypeptide [e.g., Factor VII] v. time and the bioavailability is expressed as the area under the curve (AUC). Relative bioavailability of a test preparation refers to the ratio between the AUC of the test preparation and that of the reference preparation.

In some embodiments, the preparations of the present invention exhibit a relative bioavailability of at least about 110%, preferably at least about 120%, more preferably at least about 130% and most preferably at least about 140% of the bioavailability of a reference preparation. The bioavailability may be measured in any mammalian species, preferably dogs, and the predetermined times used for calculating AUC may encompass different increments from 10 min-8 h.

"Half-life" refers to the time required for the plasma concentration of (e.g., Factor VII polypeptides of Factor VII-related polypeptides) the glycoprotein to decrease from a particular value to half of that value. Half-life may be determined using the same procedure as for bioavailability. In some embodiments, the preparations of the present invention exhibit an increase in half-life of at least about 0.25 h, preferably at least about 0.5 h, more preferably at least about 1 h, and most preferably at least about 2 h, relative to the half-life of a reference preparation.

"Immunogenicity" of a preparation refers to the ability of the preparation, when administered to a human, to elicit a deleterious immune response, whether humoral, cellular, or both. Factor VIIa polypeptides and Factor VIIa-related polypeptides are not known to elicit detectable immune responses in humans. Nonetheless, in any human subpopulation, there may exist individuals who exhibit sensitivity to particular administered proteins. Immunogenicity may be measured by quantifying the presence of anti-Factor VII antibodies and/or Factor VII-responsive T-cells in a sensitive individual, using conventional methods known in the art. In some embodiments, the preparations of the present invention exhibit a decrease in immunogenicity in a sensitive individual of at least about 10%, preferably at least about 25%, more preferably at least about 40% and most preferably at least about 50%, relative to the immunogenicity for that individual of a reference preparation.

Pharmaceutical Compositions and Methods of Use

The preparations of the present invention may be used to treat any syndrome responsive to the relevant glycoprotein. Factor VII-, FIX and FX-responsive syndromes, respectively, include syndromes such as, e.g., bleeding disorders, including, without limitation, those caused by clotting factor deficiencies (e.g., haemophilia A and B or deficiency of coagulation factors XI or VII); by thrombocytopenia or von Willebrand's disease, or by clotting factor inhibitors, or excessive bleeding from any cause. The preparations may also be administered to patients in association with surgery or other trauma or to patients receiving anticoagulant therapy.

Preparations comprising Factor VII-related polypeptides according to the invention, which have substantially reduced bioactivity relative to wild-type Factor VII, may be used as anticoagulants, such as, e.g., in patients undergoing angioplasty or other surgical procedures that may increase the risk of thrombosis or occlusion of blood vessels as occurs, e.g., in restenosis. Other medical indications for which anticoagulants are prescribed include, without limitation, deep vein thrombosis, pulmonary embolism, stroke, disseminated intravascular coagulation (DIC), fibrin deposition in lungs and kidneys associated with gram-negative endotoxemia, myocardial infarction; Acute Respiratory Distress Syndrome (ARDS), Systemic Inflammatory Response Syndrome (SIRS), Hemolytic Uremic Syndrome (HUS), MOF, and TTP.

Pharmaceutical compositions comprising the Factor VII and Factor VII-related preparations according to the present are primarily intended for parenteral administration for prophylactic and/or therapeutic treatment. Preferably, the pharmaceutical compositions are administered parenterally, i.e., intravenously, subcutaneously, or intramuscularly. They may be administered by continuous or pulsatile infusion.

Pharmaceutical compositions or formulations comprise a preparation according to the invention in combination with, preferably dissolved in, a pharmaceutically acceptable carrier, preferably an aqueous carrier or diluent. A variety of aqueous carriers may be used, such as water, buffered water, 0.4% saline, 0.3% glycine and the like. The preparations of the invention can also be formulated into liposome preparations for delivery or targeting to the sites of injury. Liposome preparations are generally described in, e.g., U.S. Pat. Nos. 4,837,028, 4,501,728, and 4,975,282. The compositions may be sterilised by conventional, well-known sterilisation techniques. The resulting aqueous solutions may be packaged for use or filtered under aseptic conditions and lyophilised, the lyophilised preparation being combined with a sterile aqueous solution prior to administration.

The compositions may contain pharmaceutically acceptable auxiliary substances or adjuvants, including, without limitation, pH adjusting and buffering agents and/or tonicity adjusting agents, such as, for example, sodium acetate, sodium lactate, sodium chloride, potassium chloride, calcium chloride, etc.

The concentration of Factor VII or Factor VII-related polypeptides in these formulations can vary widely, i.e., from less than about 0.5% by weight, usually at or at least about 1% by weight to as much as 15 or 20% by weight and will be selected primarily by fluid volumes, viscosities, etc., in accordance with the particular mode of administration selected.

Thus, a typical pharmaceutical composition for intravenous infusion could be made up to contain 250 ml of sterile Ringer's solution and 10 mg of the preparation. Actual methods for preparing parenterally administrable compositions will be known or apparent to those skilled in the art and are described in more detail in, for example, *Remington's Pharmaceutical Sciences*, 18th ed., Mack Publishing Company, Easton, Pa. (1990).

The compositions containing the preparations of the present invention can be administered for prophylactic and/or therapeutic treatments. In therapeutic applications, compositions are administered to a subject already suffering from a disease, as described above, in an amount sufficient to cure, alleviate or partially arrest the disease and its complications. An amount adequate to accomplish this is defined as "therapeutically effective amount". Effective amounts for each purpose will depend on the severity of the disease or injury as well as the weight and general state of the subject. In general, however, the effective amount will range from about 0.05 mg up to about 500 mg of the preparation per day for a 70 kg subject, with dosages of from about 1.0 mg to about 200 mg of the preparation per day being more commonly used. It will be understood that determining an appropriate dosage may be achieved using routine experimentation, by constructing a matrix of values and testing different points in the matrix.

Local delivery of the preparations of the present invention, such as, for example, topical application, may be carried out, e.g., by means of a spray, perfusion, double balloon catheters, stents, incorporated into vascular grafts or stents, hydrogels used to coat balloon catheters, or other well established methods. In any event, the pharmaceutical compositions should provide a quantity of the preparation sufficient to effectively treat the subject.

The pharmaceutical compositions of the invention may further comprise other bioactive agents, such as, e.g., non-Factor VII-related coagulants or anticoagulants.

EXPERIMENTALS

General Methods

α-Xylosidase Assay

The α-xylosidase assays are conducted in an appropriate buffer, e.g. 50 mM sodium acetate, pH 4.5, containing a suitable substrate, e.g. the O-glycopeptides that can be obtained from the O-glycopeptide map of the relevant glycoprotein (e.g., rFVIIa). The reaction is stopped after an appropriate time that can be determined experimentally, by e.g. addition of trifluoroacetic acid, and the assay mixtures are analysed by HPLC.

α-Xylosyltransferase Assay

The α-xylosyltransferase assays are conducted in an appropriate buffer, e.g. 10 mM Hepes, pH 7.2, 0.1% Triton X-100, 0.5 mM UDP-Xylose (Sigma U5875), containing a suitable substrate, e.g. the O-glycopeptides that can be obtained from the O-glycopeptide map of the relevant glycoprotein (e.g., rFVIIa) or the pyridyl-aminated oligosaccharides prepared as described in Minamida et al. (Minamida et. al., Detection of UDP-D-xylose: α-D-xyloside α1-3xylosyltransferase activity in human hepatoma cell line HepG2. J. Biochem. 120 1002-1006, 1996). The reaction is stopped after an appropriate time, that can be determined experimentally, by e.g. addition of trifluoroacetic acid, and the assay mixtures are analysed by HPLC.

The α-xylosidase and α-xylosyltransferase assays are optimized for time and, optionally for temperature and pH.
O-Glucosyltransferase Assay.

The O-glucosyltransferase assays are conducted, e.g., as described by Shao et al. (*Glycobiology* 12(11) 763-770 2002).
Factor VII Assays A suitable assay for testing for factor VIIa activity and thereby selecting suitable factor VIIa variants can be performed as a simple preliminary in vitro test. The assay is also suitable for selecting suitable factor VIIa variants.
In Vitro Hydrolysis Assay Native (wild-type) factor VIIa and factor VIIa variant (both hereafter referred to as "factor VIIa") may be assayed for specific activities. They may also be assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to factor VIIa (final concentration 100 nM) in 50 mM Hepes, pH 7.4, containing 0.1 M NaCl, 5 mM $CaCl_2$ and 1 mg/ml bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used to calculate the ratio between the activities of variant and wild-type factor VIIa:

Ratio=($A_{405\ nm}$ factor VIIa variant)/($A_{405\ nm}$ factor VIIa wild-type).

Based thereon, factor VIIa variants with an activity comparable to or higher than native factor VIIa may be identified, such as, for example, variants where the ratio between the activity of the variant and the activity of native factor VII (wild-type FVII) is around, versus above 1.0.

The activity of factor VIIa or factor VIIa variants may also be measured using a physiological substrate such as factor X, suitably at a concentration of 100-1000 nM, where the factor Xa generated is measured after the addition of a suitable chromogenic substrate (eg. 5-2765). In addition, the activity assay may be run at physiological temperature.
In Vitro Proteolysis Assay Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 microL 50 mM Hepes, pH 7.4, containing 0.1 M NaCl, 5 mM CaCl2 and 1 mg/ml bovine serum albumin, are incubated for 15 min. Factor X cleavage is then stopped by the addition of 50 microL 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used to calculate the ratio between the proteolytic activities of variant and wild-type Factor VIIa:

Ratio=($A405$ nm Factor VIIa variant)/($A405$ nm Factor VIIa wild-type).

Based thereon, factor VIIa variants with an activity comparable to or higher than native factor VIIa may be identified, such as, for example, variants where the ratio between the activity of the variant and the activity of native factor VII (wild-type FVII) is around 1, versus above 1.0.
Thrombin Generation Assay:

The ability of factor VII or factor VII-related polypeptides (e.g., variants) to generate thrombin can be measured in an assay comprising all relevant coagulation factors and inhibitors at physiological concentrations and activated platelets (as described on p. 543 in Monroe et al. (1997) Brit. J. Haematol. 99, 542-547 which is hereby incorporated as reference).
Clot Assays.
1st Generation Assay The activity of the Factor VII polypeptides may also be measured using a one-stage clot assay essentially as described in WO 92/15686 or U.S. Pat. No. 5,997,864. Briefly, the sample to be tested is diluted in 50 mM Tris (pH 7.5), 0.1% BSA and 100 μL is incubated with 100 μL of Factor VII deficient plasma and 200 μL of thromboplastin C containing 10 mM Ca2+. Clotting times are measured and compared to a standard curve using a reference standard or a pool of citrated normal human plasma in serial dilution.
2nd Generation Assay:

Essentially the same, except that recombinant human tissue factor is used instead for thromboplastin C.
Factor IX Assay
Test for Factor IX Activity:

Suitable assays for testing for factor IX activity, and thereby providing means for selecting suitable factor IX variants for use in the present invention, can be performed as simple in vitro tests as described, for example, in Wagenvoord et al., Haemostasis 1990; 20(5):276-88

Factor IX biological activity may also be quantified by measuring the ability of a preparation to correct the dotting time of factor IX-deficient plasma, e.g., as described in Nilsson et al., 1959. (Nilsson I M, Blombaeck M, Thilen A, von Francken I., Carriers of haemophilia A—A laboratory study, Acta Med Scan 1959; 165:357). In this assay, biological activity is expressed as units/ml plasma (1 unit corresponds to the amount of FIX present in normal pooled plasma.

EXAMPLES

The following examples are intended as non-limiting illustrations of the present invention.

Example 1

Preparation of α-Xylosidase by Extraction and Purification

The enzyme, α-xylosidase, can be prepared from various sources, e.g. from plant material as described by Monroe et al. (*Plant Physiology and Biochemistry* 41:877-885 (2003)). For example, plant tissues from e.g. *Arabidopsis thaliana* are ground in a mortar and pestle with quartz sand in two volumes of Buffer A (40 mM Hepes, pH 7.0, 1 M NaCl), and the filtered extract is centrifuged at 15000×g for 15 min. Ammonium sulfate is added to for example 80% saturation. Precipated proteins are collected by centrifugation at 15000×g for 15 min and redissolved in Buffer A. The α-xylosidase is purified by chromatography, for example on a Concanavalin A-Sepharose column, on an anion-exchange column and/or on other chromatographic columns known for the skilled person. Fractions are collected during elution and the fractions containing the α-xylosidase enzyme are identified by use of the α-xylosidase assay.

Example 2

Preparation of α-Xylosidase by Cloning and Expression in E. coli and Purification Genes encoding α-xylosidases, which can hydrolyse alpha xylosidic bonds, have been cloned and characterized previously and genes showing significant homology to characterized α-xylosidases have been annotated in the genomes from several prokaryotic and eukaryotic organisms. The gene sequences are available in databases such as SWISS-PROT or NCBI and can be amplified by PCR from genomic DNA from the respective organisms. Several candidates were chosen for cloning and expression in E. coli after searching protein databases for the presence of α-xylosidase proteins. The following candidate genes were selected on the basis of already existing annotation in databases (A), previous published characterization (P) or based on homology analysis to known α-xylosidases (H): gene tm0308 (*Thermotoga maritima*: A); gene bt3085 (2139 bp) and gene bt3659(2475 bp) (*Bacteroides thetaiotaomicron*: A); gene bf0551 (2238 bp) and gene bf1247 (2538 bp) (*Bacteroides fragilis*: A); gene b102681(2310 bp)(*Bacillus licheniformis*: H); gene bh1905 (2328 bp)(*Bacillus halodurans*: H), gene xylS (2196 bp)(*Sulfolobus solfataricus*: P); gene yicI (2319 bp) (*Escherichia coli*: P)

Strategy for Cloning and Expression of α-Xylosidases in E. coli

The SignalP software (Bendtsen, J. D. et al. J. Mol. Biol., 340:783-795, 2004) is used to evaluate whether a signal peptide is potentially present in the N-terminal of the candidate enzymes. BF0551, BF1247, BT3085, BT3659 are presumably secreted as indicated by a strong prediction of a signalpeptidase I cleavage site. A methionine codon encoding a start-methionine is included in front of the first amino acid following the predicted cleavage site.

Purified genomic DNA from *Bacteroides thetaiotaomicron* (ATCC 29148D), *Bacteroides fragilis* (ATCC 25285D), *Bacillus haludurans*(ATCC 21591D&BAA-125D), Sulfolobus solfataricus (ATCC 35092D), *Thermotoga maritima* (ATCC 43589D) is obtained from American Type Culture Collection. In case of E. coli (strain K-12 derivative) and *Bacillus licheniformis* (ATCC 28450), genomic DNA is prepared from bacterial cells cultivated overnight in LB medium using the DNeasy tissue kit (Qiagen) according to the manufactures instructions.

Forward and reverse primers for PCR amplification are designed with an extension in the 5'-ends comprising the restriction enzyme cleavage sites NdeI (or XbaI) and XmaI, respectively. PCR is performed using the following conditions: 1) 95° C. for 3 min: denaturation, 2) 94° C. for 30 sec: denaturation, 3) 55° C. or 60° C. for 30 sec: annealing, 4) 72° C. for 2 min: elongation. Step 2-4 is repeated for 15 cycles. PCR products are separated on 1% ethidium bromide agarose gels and bands showing the correct predicted sizes are excised from the gels and purified using the GFX DNA purification kit (Amersham Pharmacia). Purified PCR products are cloned into the pCR2.1TOPO vector according to the instructions of the manufacturer (Invitrogen). Clones showing the correct restriction enzyme cleavage profile are sequenced to evaluate the DNA sequence. The insert representing the α-xylosidase genes are released from the pCR2.1TOPO vector using the relevant restriction enzymes. A pET11a E. coli expression vector (Novagen) containing a NdeI (and XbaI) and a XmaI site is cleaved with relevant restriction enzymes and the vector part is purified as described for the PCR products. Vector and inserts are ligated together using the Rapid Ligation Kit (Roche) according to the manufacturer's instructions.

Ligation products are transformed into E. coli TOP10 (Invitrogen) cells by means of chemical transformation or heat shock methods known to the skilled persons. Cells are plated on LB/ampecillin(Amp)-medium culture plates overnight. Single colonies are selected from plates and grown overnight in LB/Amp medium. Purified pET plasmids from each colony are screened for the presence of correct inserts using restriction cleavage enzymes and evaluation of sizes of released inserts.

E. Coli Rosetta DE3 (Novagen) is transformed with pET plasmids containing the α-xylosidase genes and plated on chloramphinicol (Cam)/Amp LB plates. Cells from overnight plates are resuspended in liquid Cam/Amp LB medium and diluted to $OD_{600}$=0.1. Cells in liquid medium are propagated until $OD_{600}$=0.4-0.8. Cells are then equilibrated to a temperature of 18° C. for 30 min. and protein induction is induced with 0.5 mM IPTG o/n at 18° C. Cells are harvested and pellets are re-suspended in a buffer (e.g., 25 mM Tris HCl pH 7 or 10 mM potassium phosphate buffer pH 7) to a cell density corresponding to $OD_{600}$=~10. Cells are sonicated on ice for 3-7 times 15-30 sec with interruptions of 30 sec on ice. Cell debris is removed by centrifugation and supernatants are assayed for activity.

Assay for α-Xylosidase Activity

Supernatants resulting from sonication are evaluated on p-nitrophenyl α-D xylopyranoside (Sigma) for presence of α-xylosidase activity. Crude enzyme is incubated with 5 mM p-nitrophenyl α-D xylopyranoside at 37° C. for 1-2 hours in a buffer (e.g., 10 mM potassium buffer pH 7 or a 25 mM Tris HCl pH 7 buffer). Crude enzymes are also assayed on a fragment of human FVII comprising the Xyl-Xyl-Glc-O-Ser52 glycosylation (peptide fragment consisting of amino acid residues 39-62 of FVII) to evaluate whether the enzyme can cleave the alpha-1,3 xylosidic bonds. The incubation with peptide is performed for 3 hours or overnight at 37° C. Peptide samples incubated with or without α-xylosidase are then evaluated by MALDI MS directly after incubation to evaluate whether the enzyme can remove zero, one or two xylose sugars from the glycopeptide.

Purification of α-Xylosidases

A partial purification of the expressed α-xylosidase is performed prior to incubation with rFVII. Supernatants (from approximately 20-50 ml cell culture) obtained after cell disruption in a suitable buffer (eg. a 10 mM phosphate buffer pH 7). In case of enzymes coming from thermophiles (eg. tm0308, BH1905, XyIS), supernatants are also heated at 50-70° C. for 30 min, cooled on ice for 10 min and precipitate is removed by centrifugation for 15 min at 15.000 G in order to remove thermo-labile E. coli contaminants.

The supernatants are sterile filtrated and applied to a 1 ml DEAE FF column (Amersham Pharmacia). The purification is performed with the AKTA explorer (Amersham Pharmacia) FPLC with the following buffers: Buffer A: 25 mM sodium phosphate pH 7, Buffer B: 25 mM sodium phosphate pH 7 and 1 M NaCl. After the application is loaded, unbound sample is washed out with buffer A for 5 CV. A gradient from 0-100% buffer B is used for 20 CV during which the target protein is eluted in fractions. After purification, fractions comprising the main peak in the resulting chromatogram are assayed by incubation on p-nitrophenyl α-D xylopyranoside or by SDS PAGE. The fractions containing the α-xylosidase activity are diluted in a 20 mM Tris HCl pH 7, 2 mM $CaCl_2$ buffer and concentrated on Vivaspin 20 50.000 MWCO columns (Vivascience) by centrifugation at 2900 rpm.

O-Glycoforms of rFVIIa with Exclusively Glucose at Serine 52

The O-glycoforms of rFVIIa with exclusively glucose at serine 52 are obtained by incubation of rFVIIa in an appropriate buffer, e.g. glycylglycine or 20 mM Tris HCl pH 7.0, 2 mM $CaCl_2$, with purified α-xylosidase for an appropriate time, that can be determined experimentally. Mass spectra visualizing the deglycosylation are obtained by analysing rFVII α-xylosidase incubations ESI-MS (Q-STAR).

The resulting glycan-remodeled rFVIIa is purified from the α-xylosidase enzyme by for example anion-exchange chromatography or gel filtration or suitable combinations. The purity of the prepared O-glycoform of rFVIIa is verified by the O-glycopeptide map of rFVIIa.

Example 3

Preparation of α-Xylosidase by Cloning and Expression of T. maritima Putative α-Xylosidase Gene (Tm0308) in E. coli and Purification The above strategy (see Example 2) was followed all the way to a conclusion for tm0308. The T. maritima putative α-xylosidase gene (tm0308) was PCR amplified and cloned into a E. coli pET11a vector. Soluble tm0308 could be obtained after expression in an E. coli Rosetta (DE3) expression strain and evaluation of a crude TM0308 preparation on a p-nitrophenyl α-D xylopyranoside, clearly indicated α-xylosidase activity. The α-xylosidase was partly purified using DEAE FF chromatography followed by up-concentration by ultra filtration. The partly purified enzyme was incubated with FVII in a 25 mM Tris pH 7, 2 mM $CaCl_2$ buffer at different enzyme/FVII ratios for 3 hours at 50° C. or overnight at 37° C. Controls with identical compositions of α-xylosidase and rFVII, to which synthetic substrate was added, showed that the enzyme was active under these conditions and it was possible to visualize FVII with and without xylosidase treatment on SDS-gels and by ESI-MS. However, no significant removal of the xylose sugars linked to Glc-O-Ser52 could be detected in this first experiment. In contrast, removal of xylose from a purified reduced and alkylated FVIIa peptide comprising Xyl-Xyl-Glc-O-Ser52 was observed.

Example 4

Preparation of α-Xylosidase by Cloning and Expression in E. coli

The following constructs have been cloned into the pET expression vectors in accordance with the strategy described in Example 2: Gene b102681(2310 bp)(Bacillus licheniformis: H); gene b11905 (2328 bp)(Bacillus halodurans: H), gene xylS (2196 bp)(Sulfolobus solfataricus: P); gene yicI (2319 bp) (Escherichia coli: P).

The constructs will be expressed in Rosetta, isolated, purified, and evaluated for α-xylosidase activity in accordance with the above-described strategy.

Each α-xylosidase will be incubated with rFVIIa in an appropriate buffer, e.g. glycylglycine or 20 mM Tris HCl pH 7.0, 2 mM $CaCl_2$, for an appropriate time that can be determined experimentally and MS Spectra visualizing the deglycosylation will be obtained by analysing rFVII α-xylosidase incubations ESI-LC-MS (Q-STAR).

The resulting glycan-remodeled rFVIIa will be purified from the α-xylosidase enzyme by for example anion-exchange chromatography or gel filtration or suitable combinations thereof. The purity of the prepared O-glycoform of rFVIIa is verified by the O-glycopeptide map of rFVIIa.

Example 5

Preparation of Truncated α-Xylosidase by Cloning and Expression in E. coli

The crystal structure of YicI was recently solved. Thus, cloning of a truncated □-xylosidase enzyme representing an active, catalytical domain of the YicI protein (or other similar □-xylosidases) may be possible and is being planned, since a smaller enzyme, if active, may better access the Xyl-Xyl-Glc-O-Ser52 present in native rFVIIa. A domain comprising the active site in the enzyme is predicted from the structure. Gene sequence encoding this part of the YicI sequence is prepared from the already existing YicI pET11a plasmid for an example by PCR amplification of relevant areas of the YicI gene, The primers used for PCR will have extensions with restriction enzyme sites that can be used for ligation of the truncated YicI gene into the pET11a vector. The truncated enzyme will after expression and purification be evaluated for its potential for deglycosylation of rFVIIa as described above.

Example 6

Preparation of rFVIIa with Exclusively Xylose-Glucose at Serine 52 or Exclusively Xylose-Xylose-Glucose at Serine 52 by α-Xylosyltransferase Treatment Preparation of α-Xylosyltransferase The enzyme, UDP-D-xylose: β-D-glucoside α-1,3-D-xylosyltransferase, can be prepared from HepG2 cells as described by Omichi et al. (1997). In short, HepG2 cells are grown in a medium supplemented with 10% fetal calf serum. The microsomal fraction is prepared by homogenisation of the cells followed by centrifugation. The α-xylosyltransferase enzyme is purified by chromatography, for example on an anion-exchange column and/or on other chromatographic columns known for the skilled person. Fractions are collected during elution and the fractions containing the α-xylosyltransferase enzyme are identified by use of the α-xylosyltransferase assay.

The enzyme, UDP-D-xylose: α-D-xyloside α1,3-xylosyltransferase, can be prepared from HepG2 cells as described by Minamida et al. (1996). In short, HepG2 cells are grown in a medium supplemented 10% fetal calf serum. The microsomal fraction is prepared by homogenisation of the cells followed by centrifugation. The α-xylosyltransferase enzyme is purified by chromatography, for example on an anion-exchange column and/or on other chromatographic columns known for the skilled person. Fractions are collected during elution and the fractions containing the α-xylosyltransferase enzyme are identified by use of the α-xylosyltransferase assay.

α-Xylosyltransferase Assay

The α-xylosyltransferase assays are conducted in an appropriate buffer, e.g. 10 mM Hepes, pH 7.2, 0.1% Triton X-100, 0.5 mM UDP-Xylose (Sigma U5875), containing a suitable substrate, e.g. the O-glycopeptides that can be obtained from the O-glycopeptide map of rFVIIa or the pyridylaminated oligosaccharides prepared as described in Minamida et al. (Minamida et. al., Detection of UDP-D-xylose: α-D-xyloside α1-3xylosyltransferase activity in human hepatoma cell line HepG2. J. Biochem. 120 1002-1006, 1996). The reaction is stopped after an appropriate time, that can be determined experimentally, by e.g. addition of trifluoroacetic acid, and the assay mixtures are analysed by HPLC.

O-Glycoforms of rFVIIa with Exclusively Xylose-Glucose-at Serine 52

The O-glycoforms of rFVIIa with exclusively xylose-glucose at serine 52 are obtained by (1) treatment of rFVIIa with xylosidase as described above, (2) purification of the xylosidase treated rFVIIa from the xylosidase by for example anion-exchange chromatography, and (3) by incubation of xylosidase-treated rFVIIa in an appropriate buffer, e.g. glycylglycine, pH 7.0, 10 mM calcium chloride, with purified UDP-D-xylose: β-D-glucoside α-1,3-D-xylosyltransferase and UDP-D-xylose for an appropriate time, that can be determined experimentally. The resulting glyco-remodelled rFVIIa is purified from the UDP-D-xylose: β-D-glucoside α-1,3-D-xylosyltransferase enzyme by for example anion-exchange chromatography. The purity of the prepared O-glycoform of rFVIIa is verified by the O-glycopeptide map of rFVIIa.

O-Glycoforms of rFVIIa with Exclusively Xylose-Xylose-Glucose-at Serine 52

The O-glycoforms of with xylose-xylose-glucose at serine 52 are obtained by (1) treatment of rFVIIa with xylosidase as described above, (2) purification of the xylosidase treated rFVIIa from the xylosidase by for example anion-exchange chromatography, (3) further treatment with UDP-D-xylose: β-D-glucoside α-1,3-D-xylosyltransferase and UDP-D-xylose as described above, and (4) by incubation of the product in an appropriate buffer, e.g. glycylglycine, pH 7.0, 10 mM calcium chloride, with purified UDP-D-xylose: α-D-xyloside α1,3-xylosyltransferase and UDP-D-xylose for an appropriate time, that can be determined experimentally. The resulting glyco-remodelled rFVIIa is purified from the UDP-D-xylose: α-D-xyloside α1,3-xylosyltransferase enzyme by for example anion-exchange chromatography. The purity of the prepared O-glycoform of rFVIIa is verified by the O-glycopeptide map of rFVIIa.

Example 7

Analysis of O-Glycoform Pattern of rFVIIa

Figure 2:
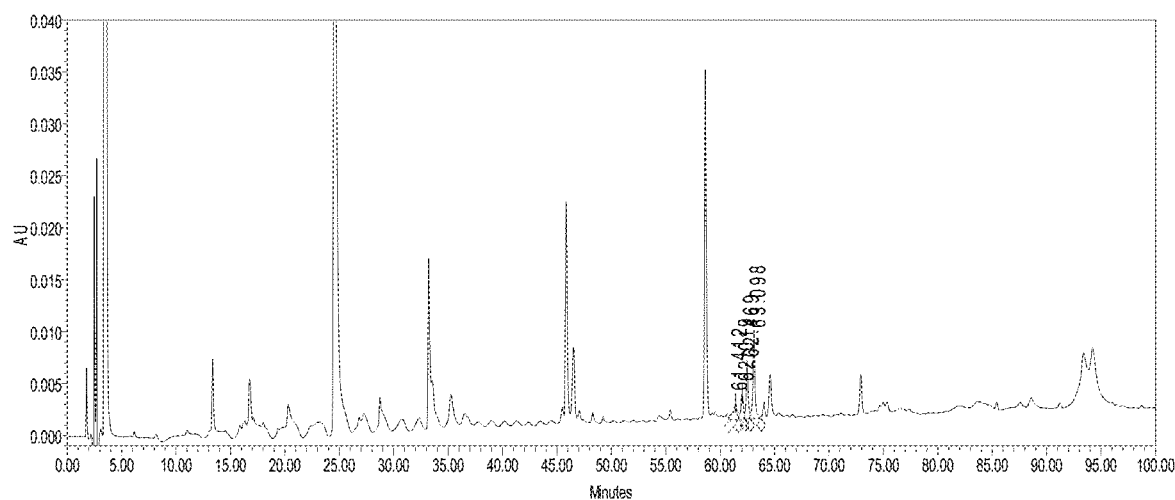
FIG. 2 shows an O-glycosylation mapping of Factor VII.

Tryptic peptide mapping of the rFVIIa light chain The relative content of the O-glycoforms of rFVIIa is determined by tryptic peptide mapping of the rFVIIa light chain. The rFVIIa is reduced and alkylated and the rFVIIa light chain is purified on a RP-HPLC column eluted with an acetonitrile gradient in water:trifluoroacetic acid. The purified rFVIIa light chain is buffer-exchanged to Tris buffer, pH 7.5 and digested with trypsin. The tryptic digest of the rFVIIa light chain is analysed on a RP-HPLC column (for example Nucleosil C18, 5μ, 300 Å, 4.0×250 mm, Macherey-Nagel 720065) eluted with an acetonitrile gradient (0%-45% acetonitrile in 100 min) in water:trifluoroacetic acid (see FIG. 2). Flow is 1.0 ml/min and detection is UV at 215 nm.

The peaks containing the O-glycopeptides of rFVIIa are eluted after approx. 60-65 min where the 1st and the 3rd peak contain O-glycopeptides with a xylose-xylose-glucose-linked to serine 52, and the 2nd and 4th peak contain O-glycopeptides with a glucose linked to serine 52.

Similarly, the 1st and the 2nd peak contain O-glycopeptides with a tetrasaccharide linked to serine 60, and the 3rd and the 4th peak contain O-glycopeptides with a fucose linked to serine 60.

Tryptic Peptide Mapping of rFVIIa

The O-glycoform pattern can be analysed by tryptic peptide mapping of rFVIIa. The rFVIIa is buffer-exchanged to Tris buffer, pH 7.5, and digested with trypsin. The tryptic digest of the rFVIIa is analysed on a RP-HPLC column (for example Nucleosil C18, 5μ, 300 Å, 4.0×250 mm, Macherey-Nagel 720065) eluted with an acetonitrile gradient (0%-45% acetonitrile in 100 min) in water:trifluoroacetic acid. Flow is 1.0 ml/min and detection is UV at 215 nm. The peaks containing the O-glycopeptides of rFVIIa are eluted after approx. 67-70 min where the 1st peak contains O-glycopeptides with a xylose-xylose-glucose linked to serine 52, and the 2nd peak contains O-glycopeptides with a glucose linked to serine 52.

Total Mass Analysis of rFVIIa

The O-glycoform pattern can be analysed by total mass analysis of rFVIIa. The rFVIIa is desalted on a Millipore ZipTip C4 column equilibrated with 1% formic acid and eluted with 3% formic acid in 90% methanol. The eluted sample is analysed by the nanospray technique on a Qstar XL mass spectrometer.

The major peak at approximately 50500 Da represents rFVIIa O-glycoforms with a glucose linked to serine 52 and the major peak at approximately 50800 Da represents rFVIIa O-glycoforms with a xylose-xylose-glucose linked to serine 52.

Example 8

Purification of Glc-O-Ser52-FVII and Xyl-Xyl-Glc-O-Ser52-FVII

Glc-O-ser52-FVII and Xyl-Xyl-Glc-O-Ser52-FVII was purified using two cycles of hydrophobic interaction chromatography (HIC). The column (1.0 cm in inner diameter× 7.0 cm length=5.5 ml column volume (CV)) packed with Toso Haas TSK-Gel phenyl 5 PW, was equilibrated with 5 CV 10 mM histidine, 10 mM CaCl2, 2.0 M NH4-acetate, pH 6.0. The column was loaded with approximately 2.5 mg of FVII pr. ml resin. To the load solution 2.0 M NH4-acetate and 10 mM CaCl2 was added prior to load. The column was washed with 5 CV 10 mM histidine, 10 mM CaCl2, 2.0 M NH4-acetate, pH 6.0. Elution was performed using a 20 CV linear gradient from 10 mM histidine, 10 mM CaCl2, 2.0 M NH4-acetate, pH 6.0 to 10 mM histidine, 10 mM CaCl2, pH 6.0. The purification was performed at a flow rate of 6 CV/h and at a temperature of 5° C. Fractions were collected during elution.

Figure 4:
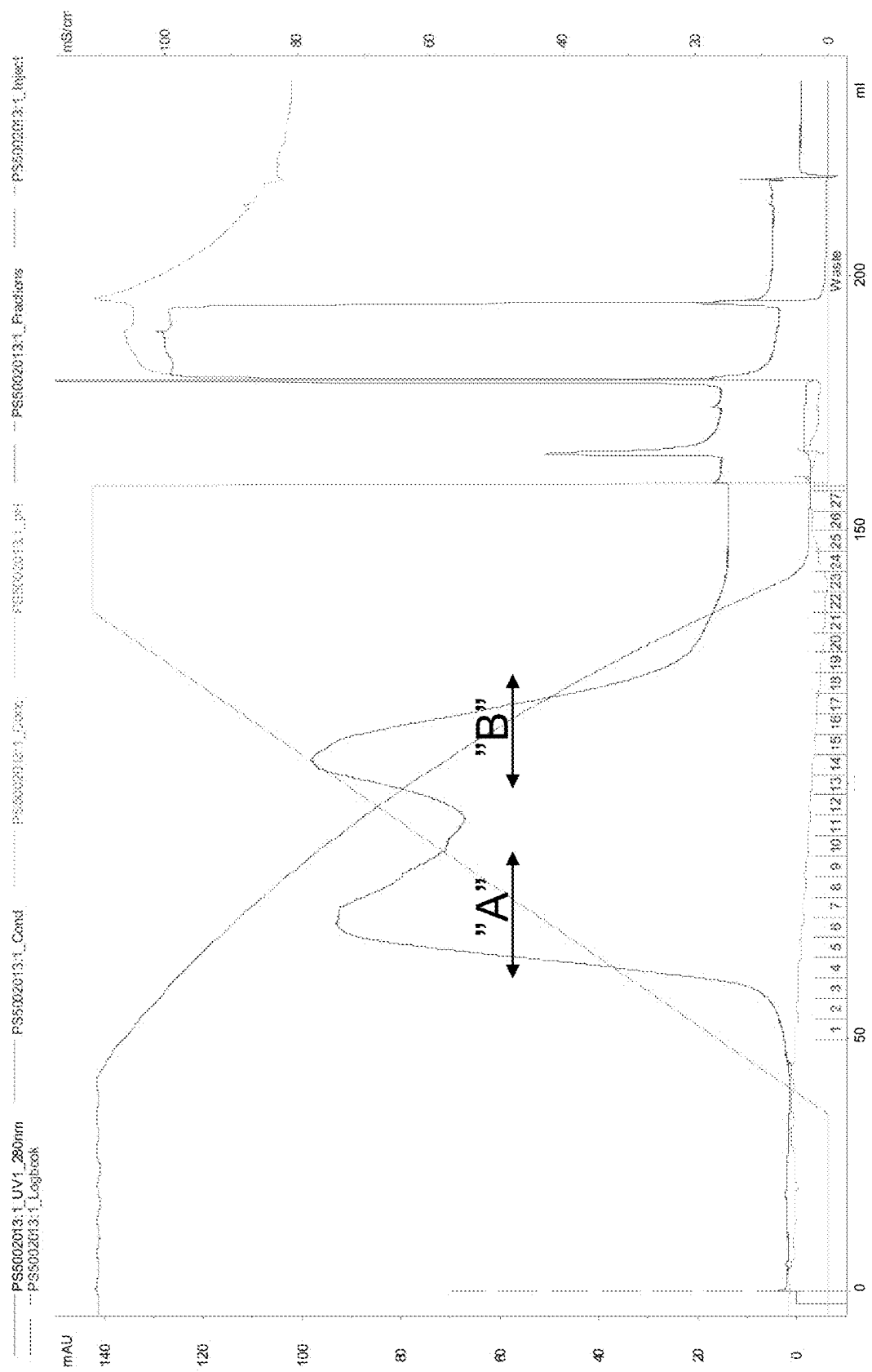
FIG. 4 shows a chromatogram from first HIC cycle showing fractions "A" and "B".
Figure 5:
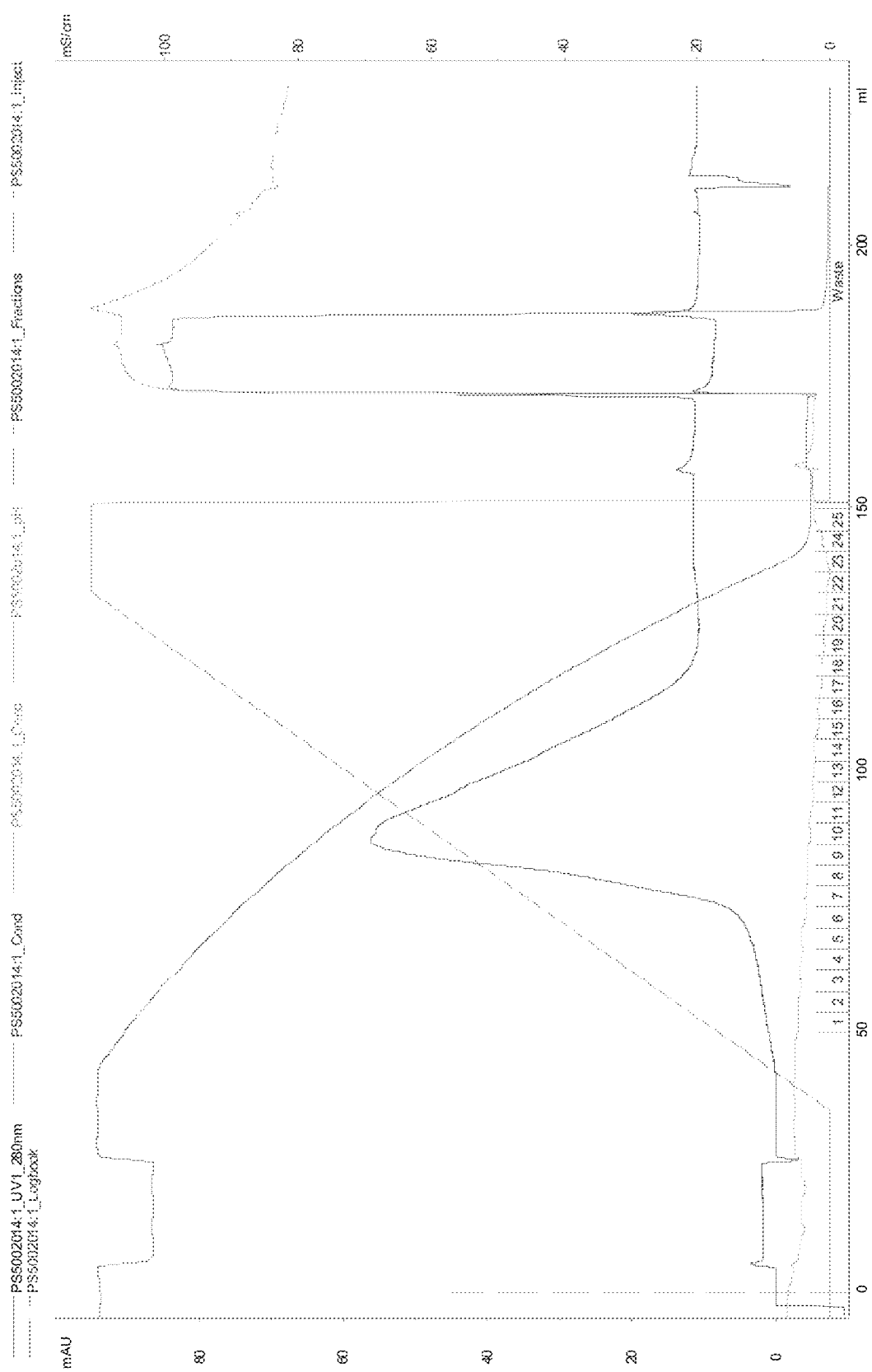
FIG. 5 shows a chromatogram obtained by reloading fraction "A" onto the HIC column; Glc-O-Ser52-FVII was identified in the peak fraction, fraction 10.
Figure 6:
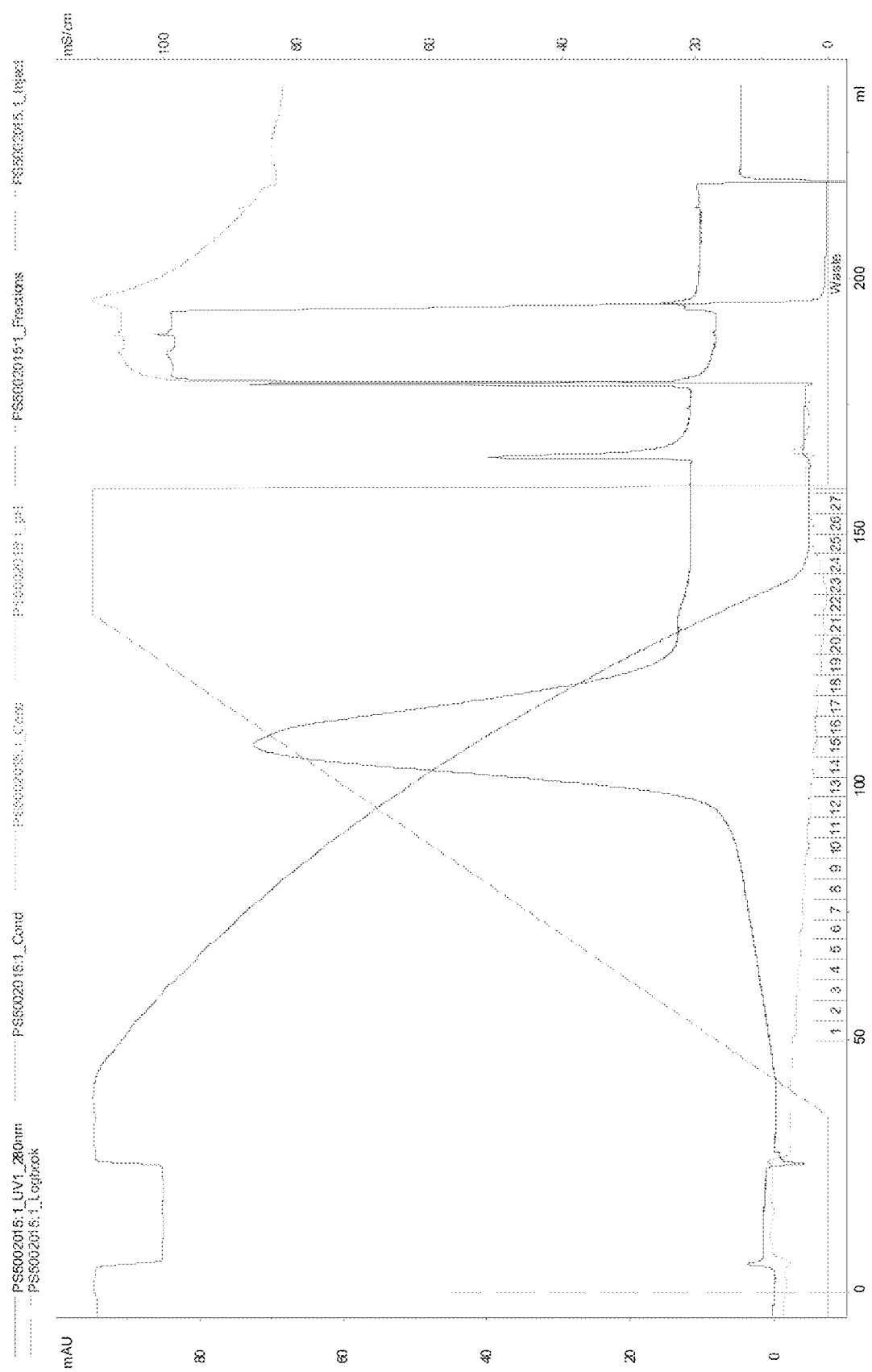
FIG. 6 shows a chromatogram obtained by reloading fraction "B" onto the HIC column; Xyl-Xyl-Glc-O-Ser52-FVII was identified in the peak fraction, fraction 15.

The FVII eluted in two overlapping major peaks (see FIG. 4: Chromatogram from first HIC cycle). Fractions containing the first peak were pooled (fraction "A", FIG. 4) and further purified by a second cycle of HIC, using the same chromatographic procedure as for the first HIC cycle (see FIG. 5: Chromatogram obtained by reloading fraction "A" onto the HIC column). Fractions containing the second major peak (fraction "B", FIG. 4) were pooled as well and further purified by a second cycle of HIC, using the same chromatographic procedure as for the first HIC cycle (see FIG. 6: Chromatogram obtained by reloading fraction "B" onto the HIC column).

Figure 7A:
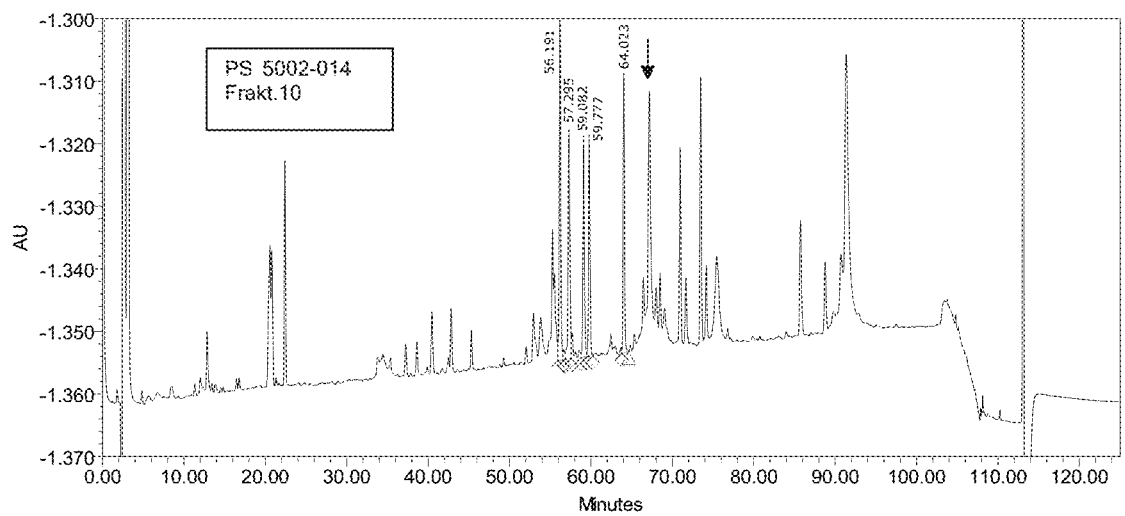
FIG. 7A shows a tryptic peptide map of the peak fraction, fraction 10; the arrow indicates the Glc-O-Ser52 O-glycopeptide.
Figure 7B:
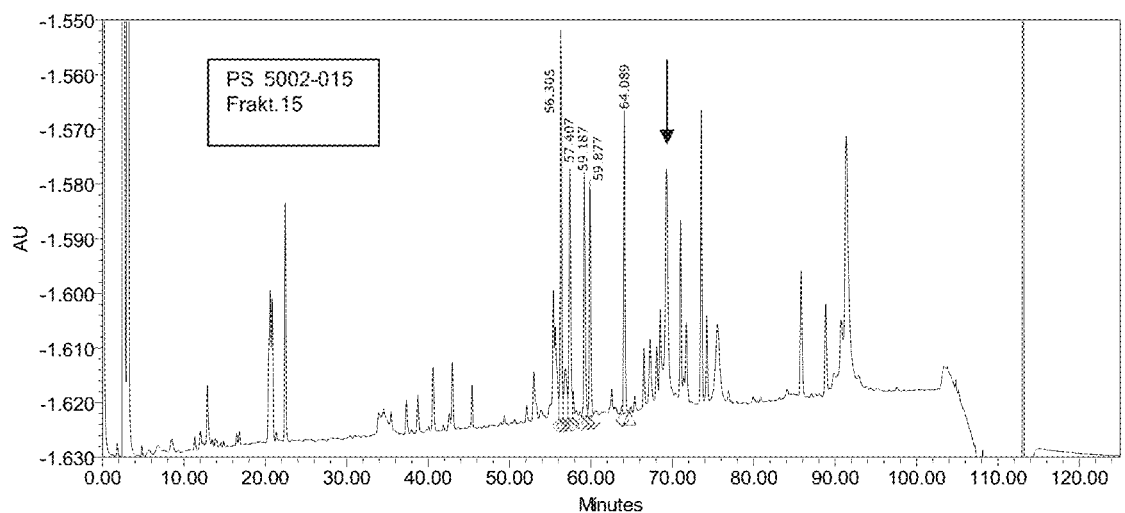
FIG. 7B shows a tryptic peptide map of the peak fraction, fraction 15; the arrow indicates the Xyl-Xyl-Glc-O-Ser52 O-glycopeptide.
Figure 8A:
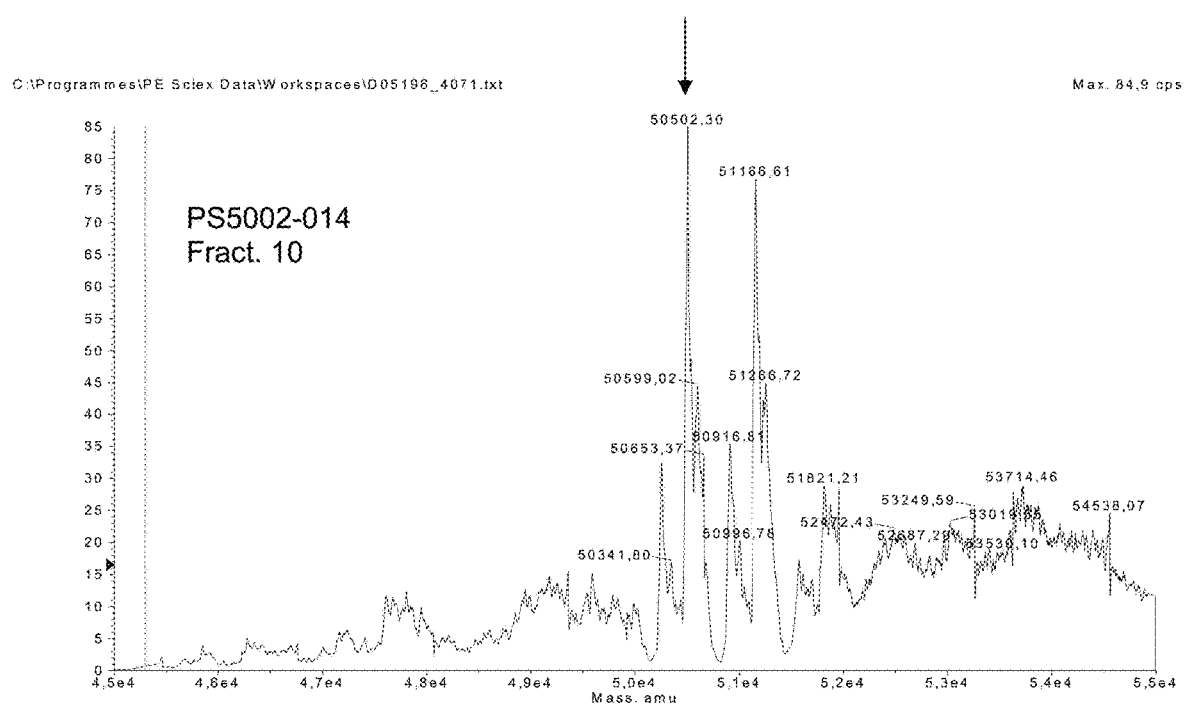
FIG. 8A shows a total mass analysis of the peak fraction, fraction 10; the arrow indicates the Glc-O-Ser52-rFVIIa O-glycoform.
Figure 8B:
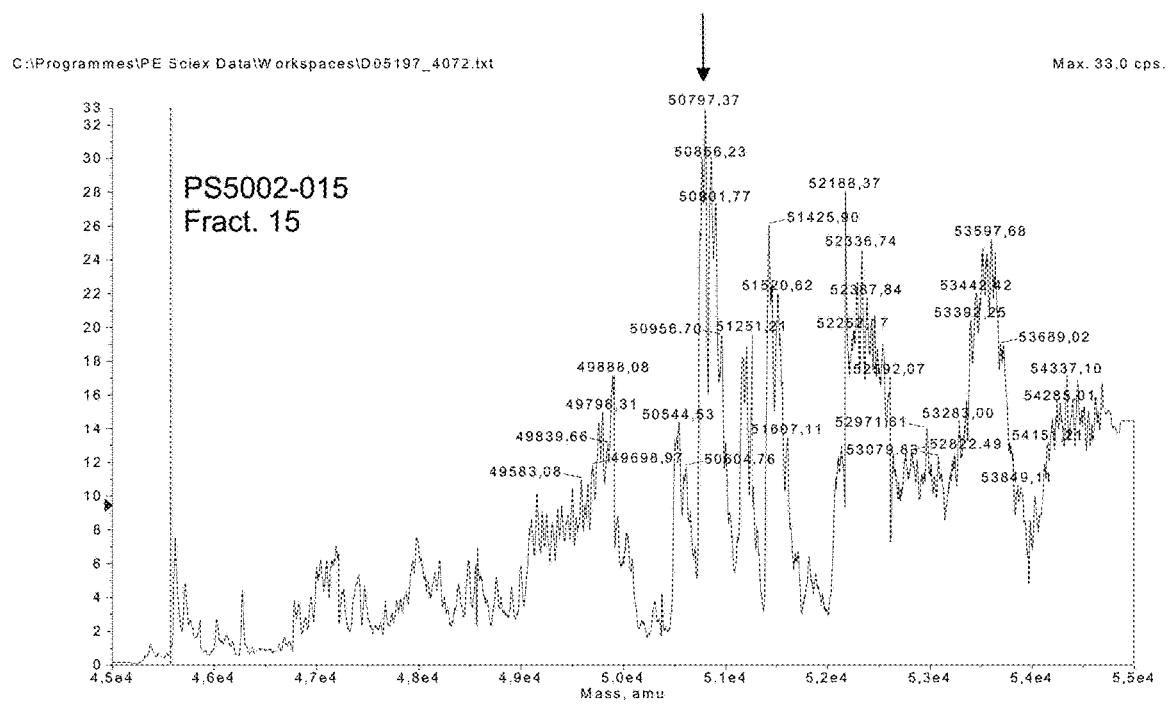
FIG. 8B shows a total mass analysis of the peak fraction, fraction 15; the arrow indicates the Xyl-Xyl-Glc-O-rFVIIa O-glycoform.

Purified Glc-O-Ser52-FVII was identified in the peak fraction, fraction 10 (FIG. 5), obtained by reloading fraction "A" onto the second HIC step. Purified Xyl-Xyl-Glc-O-Ser52-FVII was identified in the peak fraction, fraction 15 (FIG. 6), obtained by reloading fraction "B" onto the second HIC step. The identification was obtained by tryptic peptide mapping of rFVIIa as described in Example 7 (FIGS. 7A and 7B) and by total mass analysis of rFVIIa as described in Example 7 (FIGS. 8A and 8B). Both analyses showed a high content of Glc-O-Ser52-rFVIIa and a low content of Xyl-Xyl-Glc-O-Ser52-rFVIIa in the peak fraction, Fraction 10, and a low content of Glc-O-Ser52-rFVIIa and a high content of Xyl-Xyl-Glc-O-Ser52-rFVIIa in the peak fraction, Fraction 15. A quantitation of the content of the O-glycoforms in the two peak fractions could not be obtained due to relatively low rFVIIa content in the fractions (FIGS. 7A and 7B: Tryptic peptide mapping: Other peptide fragments of rFVIIa co-eluted with or eluted close to the O-glycopeptides, and the content of O-glycopeptides in low amounts could therefore not be determined.) (FIGS. 8A and 8B: Total mass analysis: Other O- and/or N-glycoforms of rFVIIa, for example N-glycoforms of rFVIIa lacking one N-acetylneuraminic acid, appeared in the mass spectra, and the content of O-glycoforms of rFVIIa in low amounts could therefore not be determined).

The specific activities of the peak fractions obtained from the HIC (Table 1) were determined by the 1st generation clotting assay. It was found that the Glc-O-Ser52-rFVIIa O-glycoform had a low specific activity while the Xyl-Xyl-Glc-O-Ser52-rFVIIa O-glycoform had a high specific activity.

TABLE 1

Specific activities determined using the 1st generation clotting assay for the peak fractions obtained from HIC. The content of rFVIIa was determined by HPLC.

| Sample | Specific activity |
| --- | --- |
| P55002-014 Frak. 10 | 44 IU/µg |
| PS5002-015 Frak. 15 | 61 IU/µg |
| PS5002-014/015 starting material | 53 IU/µg |

Example 9

Purification by Hydrophobic Interaction Chromatography

Highly purified Glc-O-Ser52-rFVIIa preparations and highly purified Xyl-Xyl-Glc-O-Ser52-rFVIIa preparations can be obtained by repeated purification on the hydrophobic interaction chromatography as described above. Highly purified Glc-O-Ser52-rFVIIa and Xyl-Xyl-Glc-O-Ser52-rFVIIa preparations with higher rFVIIa content can be obtained by increasing the amount of starting material for the hydrophobic interaction chromatography performed as described above. The content of each O-glycoform of rFVIIa in the highly purified preparations with higher rFVIIa content can be quantitated by tryptic peptide mapping of the rFVIIa light chain as described in Example 7. The specific activities of the highly purified preparations can be determined by the 1st generation clotting assay as above.

The invention claimed is:

1. A method of treating a bleeding disorder in a patient in need thereof, comprising administering to said patient a therapeutically effective amount of a pharmaceutical composition comprising:
a recombinant Factor VII polypeptide comprising the amino acid sequence of SEQ ID NO: 1, wherein at least 80% of the Factor VII polypeptides of said composition contain a Xyl-Xyl-Glc sugar chain linked, via O-linkage, to the serine residue at position 52 of SEQ ID NO:1, and a pharmaceutically acceptable carrier,
wherein said bleeding disorder is haemophilia A.

2. The method of claim 1, wherein at least 85% of the Factor VII polypeptides of said composition contain a Xyl-Xyl-Glc sugar chain linked, via O-linkage, to the serine residue at position 52 of SEQ ID NO: 1.

3. The method of claim 2, wherein said bleeding disorder is haemophilia A with inhibitors.

4. The method of claim 1, wherein at least 90% of the Factor VII polypeptides of said composition contain a Xyl-Xyl-Glc sugar chain linked, via O-linkage, to the serine residue at position 52 of SEQ ID NO: 1.

5. The method of claim 4, wherein said bleeding disorder is haemophilia A with inhibitors.

6. The method of claim 1, wherein at least 95% of the Factor VII polypeptides of said composition contain a Xyl-Xyl-Glc sugar chain linked, via O-linkage, to the serine residue at position 52 of SEQ ID NO: 1.

7. The method of claim 6, wherein said bleeding disorder is haemophilia A with inhibitors.

8. The method of claim 1, wherein at least 98% of the Factor VII polypeptides of said composition contain a Xyl-Xyl-Glc sugar chain linked, via O-linkage, to the serine residue at position 52 of SEQ ID NO: 1.

9. The method of claim 8, wherein said bleeding disorder is haemophilia A with inhibitors.

10. The method of claim 1, wherein said bleeding disorder is haemophilia A with inhibitors.

* * * * *